United States Patent [19]

Krapcho

[11] 4,456,761
[45] Jun. 26, 1984

[54] 4-SUBSTITUTED DEHYDROPROLINES

[75] Inventor: John Krapcho, Somerset, N.J.

[73] Assignee: E. R. Squibb & Sons, Inc., Princeton, N.J.

[21] Appl. No.: 403,251

[22] Filed: Jul. 29, 1982

Related U.S. Application Data

[62] Division of Ser. No. 230,206, Feb. 2, 1981, Pat. No. 4,356,182, which is a division of Ser. No. 86,905, Oct. 22, 1979, Pat. No. 4,291,040.

[51] Int. Cl.$^3$ ............................................. C07C 207/24
[52] U.S. Cl. .................................. 548/532; 546/281; 548/517; 548/527; 424/274
[58] Field of Search ................... 548/532, 517, 527; 546/281

[56] References Cited

U.S. PATENT DOCUMENTS

| | | | |
|---|---|---|---|
| 4,105,776 | 8/1978 | Ondetti et al. | 424/274 |
| 4,116,962 | 9/1978 | Ondetti et al. | 260/293.63 |
| 4,129,566 | 12/1978 | Ondetti et al. | 546/326 |
| 4,154,935 | 5/1979 | Ondetti et al. | 546/189 |
| 4,291,040 | 9/1981 | Krapcho | 424/274 X |
| 4,293,481 | 10/1981 | Condon et al. | 548/532 X |
| 4,356,182 | 10/1982 | Krapcho | 424/274 X |

Primary Examiner—Joseph Paul Brust
Attorney, Agent, or Firm—Lawrence S. Levinson; Stephen B. Davis

[57] ABSTRACT

Compounds of the formula

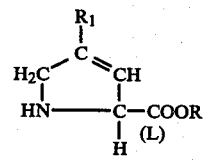

are useful as intermediates in the preparation of various hypotensive agents.

3 Claims, No Drawings

4-SUBSTITUTED DEHYDROPROLINES

This application is a division of Ser. No. 230,206 filed Feb. 2, 1981 now U.S. Pat. No. 4,356,182 which in turn is a division of Ser. No. 86,905 filed Oct. 22, 1979, now U.S. Pat. No. 4,291,040.

BACKGROUND OF THE INVENTION

Mercaptoacyl derivatives of proline and 4-hydroxyproline are disclosed as useful antihypertension agents due to their angiotensin converting enzyme inhibition activity in U.S. Pat. No. 4,105,776 of Ondetti et al.

Mercaptoacyl derivatives of proline wherein the acyl sidechain can be substituted by an alkyl or trifluoromethyl group and the proline can be substituted with one or more halogens are also useful as angiotensin converting enzyme inhibitors as note Ondetti et al. U.S. Pat. No. 4,154,935.

Mercaptoacyl 3,4-dehydroprolines are disclosed as useful antihypertension agents due to their angiotensin converting enzyme inhibition activity in U.S. Pat. No. 4,129,566 of Ondetti et al.

Mercaptoacyl derivatives of proline wherein the acyl sidechain can be substituted with a lower alkylthio group are also disclosed as angiotensin converting enzyme inhibitors by Ondetti et al. in U.S. Pat. No. 4,116,962.

SUMMARY OF THE INVENTION

This invention relates to new mercaptoacyl 4,4-disubstituted prolines of formula I and salts thereof

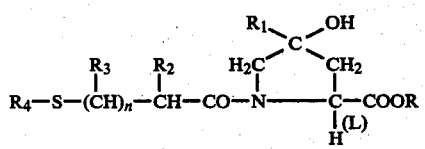

and mercaptoacyl 4-substituted dehydroproline compounds of formula II and salts thereof

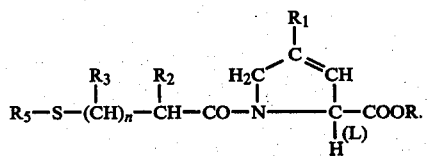

R in both formulas represents hydrogen or lower alkyl.

$R_1$ in both formulas represents lower alkyl, lower alkenyl, lower alkynyl,

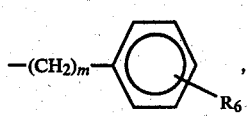

—$(CH_2)_m$-cycloalkyl, α-naphthyl, β-naphthyl,

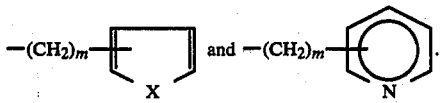

$R_2$ and $R_3$ in both formulas are independently selected from hydrogen, lower alkyl, lower alkylthio, and halo substituted lower alkyl.

n in both formulas is zero, one or two.

$R_4$ is hydrogen, a hydrolyzably removable protecting group, a chemically removable protecting group, or

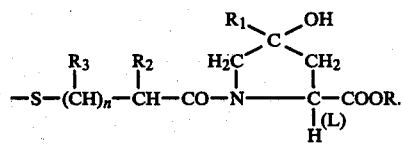

$R_5$ is hydrogen, a hydrolyzable removable protecting group, a chemically removable protecting group, or

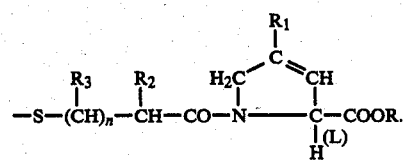

m is zero, one, two or three.

$R_6$ is hydrogen, lower alkyl of 1 to 4 carbons, especially methyl, lower alkoxy of 1 to 4 carbons, especially methoxy, lower alkylthio of 1 to 4 carbons, especially methylthio, chloro, bromo, fluoro, trifluoromethyl or hydroxy. The hydroxy substituted compounds are obtained by heating the corresponding methoxy substituted compound with pyridine HCl.

X is oxygen or sulfur.

DETAILED DESCRIPTION OF THE INVENTION

The invention in its broadest aspects relates to the mercapto 4,4-disubstituted prolines and the mercaptoacyl-4-substituted dehydroproline compounds of formulas I and II above, to compositions containing such compounds and to the method for using such compounds as anti-hypertensive agents. This invention is also directed to certain novel intermediates useful in the preparation of compounds of formulas I and II.

The term lower alkyl as used in defining the symbols R, $R_1$, $R_2$ and $R_3$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl being most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclohexyl being most preferred.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term lower alkenyl as used in defining the symbol $R_1$ are mono-unsaturated straight or branched chain hydrocarbon groups of from 2 to 7 carbons such as ethenyl, propenyl, isopropenyl, butenyl, and the like. The lower alkynyl groups are straight or branched chain hydrocarbon groups of from 2 to 7 carbons having one triple bond, e.g., propargyl. The preferred lower alkenyl groups are from 2 to 5 carbons and the preferred lower alkynyl groups are from 2 to 4 carbon atoms.

The term hydrolyzably removable protecting group employed in defining $R_4$ and $R_5$ refers to a group that can be removed by conventional hydrolysis or ammonolysis. Acyl groups of the formula

are suitable for this purpose wherein $R_7$ can be lower alkyl of 1 to 6 carbons, lower alkyl substituted with one or more chloro, bromo or fluoro groups, $-(CH_2)_m-$ cycloalkyl, an aryl group such as

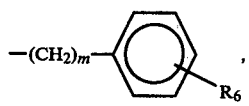

a hetero group such as

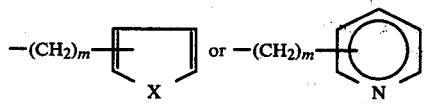

wherein m, $R_6$ and X are as defined above. Preferred protecting groups are the lower alkanoyl groups having up to four carbons, especially acetyl, and benzoyl.

The term chemically removable protecting group employed in defining $R_4$ and $R_5$ refers to groups such as p-methoxybenzyl, p-methoxybenzyloxycarbonyl, t-butoxycarbonyl, etc. These groups can be removed without effecting the remainder of the molecule such as by treament with trifluoroacetic acid and anisole.

As shown in formulas I and II, the asymmetric center in the proline or dehydroproline ring is in the L-configuration. Of course, an additional asymmetric center can be present in the mercapto sidechain depending upon the substituents $R_2$ and $R_3$. The products of formulas I and II can accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in the final product can be separated by conventional chromatographic or fractional crystallization methods. Preferably, if there is an asymmetric center in the mercaptoacyl sidechain, it is in the D-configuration.

Preferred compounds of formulas I and II are those wherein R is hydrogen; $R_1$ is lower alkyl of 1 to 4 carbons or

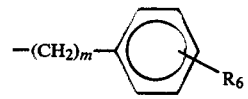

wherein m is zero, one or two, and $R_6$ is hydrogen, methyl, methoxy methylthio, chloro, fluoro, trifluoromethyl or hydroxy; $R_2$ is hydrogen, methyl, trifluoromethyl, or methylthio; $R_3$ is hydrogen; n is zero or one; and $R_4$ or $R_5$ is hydrogen. Also preferred as intermediates are the above compounds wherein $R_4$ or $R_5$ is acetyl or benzoyl, especially acetyl.

Most preferred are the above compounds wherein $R_1$ is phenyl; $R_2$ is hydrogen or methyl, especially methyl; $R_3$ is hydrogen; n is one; and $R_4$ or $R_5$ is hydrogen.

The compounds of formula I are obtained by coupling the 4,4-disubstituted proline of the formula

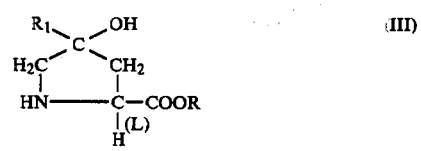

with an acid or its chemical equivalent of the formula

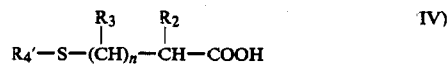

wherein $R'_4$ is hydrogen, $R_7$—CO—, or a chemically removable protecting group to yield the product of the formula

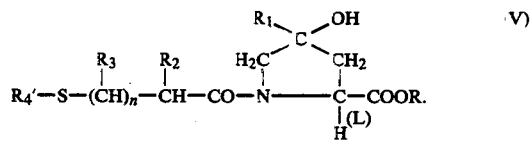

This reaction can be effected in the presence of a coupling agent such as dicyclohexylcarbodiimide or the like, or the acid can be activated by formation of its mixed anhydride, symmetrical anhydride, acid halide, active ester or use of Woodward reagent K, N-ethoxycarbonyl-2-ethoxy-1,2-dihydroquinoline or the like. For a review of the methods of acylation, see Methoden der Organishchen Chemie (Houben-Weyl), Vol. XV, part II, page 1 et seq. (1974). Preferably, the acid halide, especially the acid chloride, of formula IV is reacted with the acid of formula III.

If the proline of formula III is reacted in the ester form the resulting ester product of formula V, i.e., R is alkyl, can be converted to the free acid, i.e., R is hydrogen, by conventional means. For example, if R is t-butyl this ester protecting group can be removed by saponification.

The product of formula V is preferably isolated and purified by crystallization, e.g., by forming the dicyclohexylamine salt and then converting the salt to the free acid form by treatment with an aqueous solution of an acid, such as potassium acid sulfate.

The product of formula V bearing the acyl group $R_7$—CO— can be converted to the products of formula I wherein $R_4$ is hydrogen by conventional hydrolysis or by ammonolysis.

The products of formula I wherein $R_4$ is $$-S-(CH)_n-\underset{R_3}{\underset{|}{C}}H-CO-N\underset{\underset{H}{|(L)}}{\overset{H_2C\underset{|}{\overset{R_1}{\underset{|}{C}}}\underset{|}{\overset{OH}{}}CH_2}{\underset{|}{\underset{|}{\underset{|}{|}}}}}C-COOR$$

are obtained by directly oxidizing with iodine a product of formula I wherein $R_4$ is hydrogen.

The esters of formula I wherein R is lower alkyl can be obtained from the carboxylic acid compounds, i.e., wherein R is hydrogen, by conventional esterification procedures, e.g., by esterification with a diazoalkane such as diazomethane, a 1-alkyl-3-p-tolyltriazene, such as 1-n-butyl-3-p-tolyltriazene, or the like.

The 4-disubstituted proline intermediate of formula III is prepared by reacting the N-protected 4-keto proline of the formula $$\text{protected-N}\underset{\underset{H}{|(L)}}{\overset{H_2C\overset{O}{\overset{\|}{C}}CH_2}{\underset{|}{\underset{|}{|}}}}C-COOR$$

with a solution of the Grignard or lithium reagent $$R_1-\text{Mg-halo or } R_1\text{-Li} \qquad (VII)$$

wherein halo is Br or Cl and the N-protecting group is carbobenzyloxy or other suitable acyl protecting groups, to yield $$\text{protected-N}\underset{\underset{H}{|(L)}}{\overset{H_2C\overset{R_1}{\underset{|}{C}}\overset{OH}{}CH_2}{\underset{|}{\underset{|}{|}}}}C-COOR \qquad (VIII)$$

The product of formula VIII will usually be obtained as a mixture of cis- and trans-hydroxy isomers with respect to the carboxylic acid or ester group.

This mixture can be separated into the individual cis-hydroxy and trans-hydroxy isomers at this point of the synthetic procedure and the isomers can be purified by crystallization, by conversion to a salt form such as the 1-adamantanamine salt, or by chromatographic means. Alternatively, the mixture of cis and trans isomers can be carried through to yield the compounds of formula V or formula I as a cis-trans mixture. Chromatographic separation could then be performed as the last step of the synthesis.

The N-protecting group can be removed from the intermediate of formula VIII by hydrogenation in the presence of a palladium-carbon catalyst to yield the 4,4-disubstituted proline of formula III.

The compounds of formula II are obtained by coupling the 4-substituted dehydroproline of the formula $$HN\underset{\underset{H}{|(L)}}{\overset{H_2C\overset{R_1}{\underset{\|}{C}}CH}{\underset{|}{\underset{|}{|}}}}C-COOR \qquad (IX)$$

with the acid or chemical equivalent of the formula $$R_5'-S-(CH)_n-\underset{R_3}{\underset{|}{C}}H-COOH \qquad (X)$$

wherein $R'_5$ is hydrogen, $R_7$—CO—, or a chemically removable protecting group to yield the product of the formula $$R_5'-S-(CH)_n-\underset{R_3}{\underset{|}{C}}H-CO-N\underset{\underset{H}{|(L)}}{\overset{H_2C\overset{R_1}{\underset{\|}{C}}CH}{\underset{|}{\underset{|}{|}}}}C-COOR \qquad (XI)$$

As above, this reaction can be performed in the presence of a coupling agent such as dicyclohexylcarbodiimide or the like, or the acid can be activated by formation of its mixed anhydride, symmetrical anhydride, acid halide, active ester or use of Woodward reagent, K, N-ethoxycarbonyl-2-ethoxy-1,2-dihydroquinoline or the like. Preferably, the acid halide, especially the acid chloride, of formula X is reacted with the acid of formula IX.

If the dehydroproline of formula IX is reacted in the ester form the resulting ester product of formula XI, i.e., R is alkyl, can be converted to the free acid, i.e., R is hydrogen, by conventional means. For example, if R is t-butyl treatment with trifluoroacetic acid and anisole gives the free acid.

The product of formula XI is preferably isolated and purified by crystallization, e.g., by forming the dicyclohexylamine salt and then converting the salt to the free acid form by treatment with an aqueous solution of an acid, such as potassium acid sulfate.

The product of formula XI bearing the acyl group $R_7$—CO— can be converted to the products of formula II wherein $R_5$ is hydrogen by conventional hydrolysis or by ammonolysis.

The products of formula II wherein $R_5$ is $$-S-(CH)_n-\underset{R_3}{\underset{|}{C}}H-CO-N\underset{\underset{H}{|(L)}}{\overset{H_2C\overset{R_1}{\underset{\|}{C}}CH}{\underset{|}{\underset{|}{|}}}}C-COOR$$

are obtained by directly oxidizing with iodine a product of formula II wherein $R_5$ is hydrogen.

The esters of formula II wherein R is lower alkyl can be obtained from the carboxylic acid compounds, i.e., wherein R is hydrogen, by conventional esterification procedures, e.g., by esterification with a diazoalkane such as diazomethane, a 1-alkyl-3-p-tolyltriazene, such as 1-n-butyl-3-p-tolyltriazene, or the like.

The 4-substituted dehydroprolines of formula IX are obtained from the N-protected 4,4-disubstituted prolines of formula VIII. The intermediate of formula VIII is treated with a dehydrating agent such as p-toluenesulfonic acid, sulfuric acid, or potassium bisulfate to yield

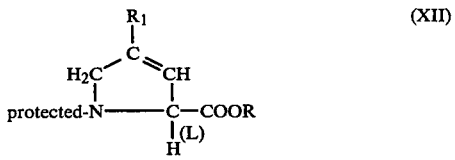

The N-protecting group and ester protecting group can then be removed by conventional procedures to yield the dehydroproline of formula IX. Alternatively, the dehydroproline of formula IX can be obtained in a single step by treating the N-protected 4,4-disubstituted proline of formula VIII with a mixture of concentrated HCl and acetic acids and then neutralizing with ammonia.

The compounds of this invention form basic salts with a variety of inorganic or organic bases. The salt forming ion derived from such bases can be metal ions, e.g., aluminum, alklai metal ions, such as sodium or potassium, alkaline earth metal ions such as calcium or magnesium, or an amine salt ion, of which a number are known for this purpose, for example, aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of formulas I and II wherein R4 and R5 are hydrogen,

or the disulfide type substituent, especially wherein R4 and R5 are hydrogen, are useful as hypotensive agents. They inhibit the conversion of the decapeptide angiotensin I to angiotensin II and, therefore, are useful in relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of formulas I and II angiotensin dependent hypertension in the species of mammal suffering therefrom is alleviated. A single does, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount—which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methchlothiazide, trichloromethiazide, polythiazide or benzthiazide, as well as ethacrynic acid, tricrynafen, chlorthalidone, furosemide, musolimine, bumetanide, triamterene, amiloride and spironolactone, and salts of such compounds.

The compounds of formulas I and II can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

[1(S),4R]-1-[3-(Acetylthio)-2-methyl-1-oxopropyl]-4-hydroxy-4-phenyl-L-proline (a)

N-Carbobenzyloxy-cis-4-hydroxy-trans-4-phenyl-L-proline

65 Ml. of 3.2M phenylmagnesium bromide in ether (0.21 mole) is added to a stirred solution of 23.8 g. (0.09 mole) of N-carbobenzyloxy-4-keto-L-proline (prepared according to Patchett et al., J. Amer. Chem. Soc., Vol. 79, p. 189–192) in 700 ml. of tetrahydrofuran over a period of 15 minutes while the temperature is maintained at 20°–25°. A gelatinous precipitate begins to separate after 45 ml. of the Grignard solution is added. After stirring overnight, most of the precipitate dissolves. The mixture is cooled to 15°, treated with a solution of 25 g. of ammonium chloride in 250 ml. of ice-water, stirred for one hour, and acidified with 35 ml. of 6N hydrochloric acid. The organic phase is separated and the aqueous layer is extracted twice with 200 ml. of ethyl acetate. The organic phases are combined, dried (MgSO$_4$), filtered, and the solvent evaporated to give 32 g. of tan foam-like solid. This material is treated with 200 ml. of ether—125 ml. of N sodium hydroxide, shaken in a separatory funnel and filtered to remove the gelatinous material at the interface. The aqueous phase is separated, acidified with 22 ml. of 6N hydrochloric acid and extracted with 100 ml. of ethyl acetate. The layers are separated and the aqueous phase is extracted twice with 50 ml. ethyl acetate. The organic phases are combined, dried (MgSO$_4$), filtered and the solvent evaporated to give 27.3 g. of a pale yellow foam-like residue. This material is treated with 150 ml. of ether to give a solution from which the product crystallizes. After cooling overnight, the mixture is filtered to give 11.8 g. of colorless solid; m.p. 120°–122°. Crystallization from 22 ml. of ethyl acetate—22 ml. of hexane yields 10.1 g. of N-carbobenzyloxy-cis-4-hydroxy-trans-4-phenyl-L-proline; m.p. 121°–123°; $[\alpha]_D^{25}$ −32° (c, 1% in CHCl$_3$). Additional product can be obtained by concentrating and cooling of the filtrate.

Anal: Calc'd. for C$_{19}$H$_{19}$NO$_5$: C, 66.85; H, 5.61; N, 4.10 Found: C, 66.67; H, 5.50; N, 3.99.

(b) cis-4-Hydroxy-trans-4-phenyl-L-proline

A solution of 3.0 g. (0.008 mole) of N-carbobenzyloxy-cis-4-hydroxy-trans-4-phenyl-L-proline from part (a) in 120 ml. of 2:1 methanol-water is treated with 1.0g. of 5% palladium carbon catalyst and placed under 49 psi. of hydrogen. The uptake of hydrogen is rapid (almost complete after one hour). After three hours, the catalyst is filtered through Celite, washed with methanol and the filtrate concentrated on a rotary evaporator to yield 1.75 g. of light gray solid cis-4-hydroxy-trans-4-phenyl-L-proline; m.p. 240°–242°; $[\alpha]_D^{25}$ +15° (c, 1% in N HCl).

Anal: Calc'd. for C$_{11}$H$_{13}$NO$_3$.0.5 H$_2$O: C, 61.10; H, 6.53; N, 6.48, Found: C, 61.06; H, 6.55; N, 6.31.

(c)
[1(S),4R]-1-[3-(Acetylthio)-2-methyl-1-oxopropyl]-4-hydroxy-4-phenyl-L-proline A stirred suspension of 4.3 g. (0.02 mole) of cis-4-hydroxy-trans-4-phenyl-L-proline from part (b) in 50 ml. of water and 2 g. of sodium carbonate is cooled to 5° and treated dropwise with a solution of 3.6 g. of D-3-acetylthio-2-methylpropionyl chloride in 5 ml. of ether over a period of ten minutes. An additional 2.0 g. of sodium carbonate is added during this period to maintain the pH at 8. After stirring for 90 minutes at room temperature, the solution is cooled, acidified with 6N hydrochloric acid and extracted with 50 ml. of ethyl acetate. The layers are separated and the aqueous phase is extracted three times with 25 ml. of ethyl acetate. The organic phases are combined, dried (MgSO$_4$), filtered, and the solvent evaporated to give 7.0 g. of nearly colorless foam-like solid. This material is treated with 50 ml. of ethyl acetate at room temperature and then cooled to give 5.35 g. of colorless [1(S),4R]-1-[3-(acetylthio)-2-methyl-1-oxopropyl]-4-hydroxy-4-phenyl-L-proline. A small sample is crystallized from ethyl acetate; m.p. 177°–179°; $[\alpha]_D^{25}$ −111° (c, 1% in ethanol).

Anal. Calc'd. for C$_{17}$H$_{21}$NO$_5$S: C, 58.10; H, 6.02; N, 3.99; S, 9.12, Found. C, 58.30; H, 5.99; N, 3.88; S, 9.21.

EXAMPLE 2

[1(S),4R]-4-Hydroxy-1-(3-mercapto-2-methyl-1-oxopropyl)-4-phenyl-L-proline 5.1 g. (0.015 mole) of [1(S),4R]-1-[3-(Acetylthio)-2-methyl-1-oxopropyl]-4-hydroxy-4-phenyl-L-proline, under argon, is treated with 10 ml. of concentrated ammonia in 25 ml. of water. The stirred mixture becomes a solution in several minutes and is allowed to stand for two hours at room temperature. The solution is then cooled and extracted twice with 20 ml. of ethyl acetate. The aqueous phase is layered with 20 ml. of ethyl acetate, acidified with 6N hydrochloric acid and the layers separated. The aqueous phase is extracted twice with 20 ml. of ethyl acetate. The organic phases are combined, dried (MgSO$_4$), filtered and the solvent evaporated to give 4.8 g. of foam-like product. This material is dissolved in 10 ml. of ethyl acetate and diluted with 10 ml. of hexane. The material initially separates as an oil and then crystallizes. After cooling overnight, the colorless solid is filtered under argon and dried to yield 4.1 g. of [1(S),4R]-4-hydroxy-1-(3-mercapto-2-methyl-1-oxopropyl)-4-phenyl-L-proline; m.p. 152°–154°; $[\alpha]_D^{25}$ −57° (c, 1% in ethanol).

Anal: Calc'd. for C$_{15}$H$_{19}$NO$_4$S.0.25 H$_2$O: C, 57.48; H, 6.27; N, 4.47; S, 10.23; SH, 10.02, Found: C, 57.81; H, 6.24; N, 4.41; S, 10.14; SH, 9.90.

EXAMPLE 3

[1(S),2S]-1-[(3-Acetylthio)-2-methyl-1-oxopropyl]-2,5-dihydro-4-phenyl-1H-pyrrole-2-carboxylic acid (a) 3,4-Dehydro-4-phenyl-L-proline A mixture of 8.0 g. of N-carbobenzyloxy-cis-4-hydroxy-trans-4-phenyl-L-proline from Example 1(a) in 125 ml. of glacial acetic acid and 50 ml. of concentrated hydrochloric acid is stirred at room temperature (CO$_2$ is evolved) and then refluxed for one hour. The resulting pale brown solution is concentrated on a rotary evaporator and the residual oil is dissolved in 50 ml. of acetonitrile. The solvent is removed in vacuo and the granular residue is triturated with 100 ml. of ether and filtered to give 6.0 g. of brown solid, m.p. 130°–135° (dec.). This material is suspended in 12 ml. of water and neutralized with 7N ammonia-water. The mixture is cooled, filtered, and the solid is washed with cold water to give 2.1 g. of tan 3,4-dehydro-4-phenyl-L-proline; m.p. 245°–247° (dec.); $[\alpha]_D^{25}$ −56° (c, 1% in 1N HCl).

Anal. Calc'd. for C$_{11}$H$_{11}$NO$_2$: C, 69.82; H, 5.86; N, 7.40, Found: C, 69.00; H, 5.73; N, 7.27.

(b)
[1(S),2S]-1-[3-(Acetylthio)-2-methyl-1-oxopropyl]-2,5-dihydro-4-phenyl-1H-pyrrole-2-carboxylic acid A stirred mixture of 2.0 g. (0.01 mole) of 3,4-dehydro-4-phenyl-L-proline from part (a) in 25 ml. of water and 1.5 g. of sodium carbonate is cooled to 12° and treated dropwise with a solution of D-3-acetylthio-2-methylpropionyl chloride in 5 ml. of ether over a period of ten minutes. An additional 0.5 g. of sodium carbonate is added during this period to maintain the pH at 8. The ice bath is removed and the mixture is allowed to stir for 90 minutes at room temperature. The solution is cooled, acidified with 6N hydrochloric acid and extracted with 25 ml. of ethyl acetate—25 ml. of chloroform. The layers are separated and the aqueous phase is extracted three times with 25 ml. of chloroform. The organic phases are combined, dried (MgSO$_4$), filtered and the solvent evaporated to give 4.7 g. of a residual syrup. This syrup is dissolved in 30 ml. of ethyl acetate and treated with a solution of 2.0 g. of dicyclohexylamine in 10 ml. of ethyl acetate. The salt slowly crystallizes from solution. After cooling overnight, the colorless solid is filtered and dried to give 3.3 g. of the dicyclohexylamine salt; m.p. 178°–180° (s. 180°). This material is recrystallized from 90 ml. of acetonitrile to give 2.85 g. of colorless [1(S),2S]-1-[(3-acetylthio)-2-methyl-1-oxopropyl]-2,5-dihydro-4-phenyl-1H-pyrrole-2-carboxylic acid, dicyclohexylamine salt; m.p. 182°–184° (dec.); $[\alpha]_D^{25} - 138°$ (c, 1% in ethanol).

Anal: Calc'd. for C$_{17}$H$_{19}$NO$_3$S.C$_{12}$H$_{13}$N: C, 67.67; H, 8.23; N, 5.44; S, 6.23, Found: C, 67.59; H, 8.33; N, 5.28; S, 6.09.

The above dicyclohexylamine salt is suspended in 30 ml. of ethyl acetate, cooled and treated with 30 ml. of 10% potassium bisulfate. 10 Ml. of chloroform are added and the mixture is shaken. The layers are separated and the aqueous phase is extracted twice with 30 ml. of ethyl acetate. The organic phases are combined, dried (MgSO$_4$), filtered and the solvent evaporated to give 2.2 g. of foam-like colorless [1(S),2S]-1-[3-(acetylthio)-2-methyl-1-oxopropyl]-2,5-dihydro-4-phenyl-1H-pyrrole-2-carboxylic acid.

EXAMPLE 4

[1(S),2S]-2,5-Dihydro-1-(3-mercapto-2-methyl-1-oxopropyl)-4-phenyl-1H-pyrrole-2-carboxylic acid 2.2 g. of [1(S),2S]-1-[(3-Acetylthio)-2-methyl-1-oxopropyl]-2,5-dihydro-4-phenyl-1H-pyrrole-2-carboxylic acid from Example 3, under argon, is treated with a cold solution of 8 ml. of concentrated ammonia in 20 ml. of water. The stirred mixture becomes a solution in several minutes and is allowed to stand for two hours at room temperature. The solution is cooled and extracted twice with 20 ml. of ethyl acetate. The aqueous phase is layered with 20 ml. of ethyl acetate, acidified with 6N hydrochloric acid and the layers separated. The aqueous phase is extracted twice with 20 ml. of ethyl acetate. The organic phases are combined, dried (MgSO$_4$), filtered and the solvent evaporated to give 1.52 g. of a colorless foam-like solid; m.p. 90°–95° (s. 45°). This is suspended in 25 ml. of hexane and filtered to give 1.35 g. of solid, m.p.; 90°–95° (s. 60°). This material is dissolved in 50 ml. of ethyl acetate and extracted three times with 5 ml. of water under argon to yield 1.1 g. of colorless foam-like solid [1(S),2S]-2,5-dihydro-1-(3-mercapto-2-methyl-1-oxopropyl)-4-phenyl-1H-pyrrole-2-carboxylic acid; m.p. 90°–95° (s. 60°); $[\alpha]_D^{25} - 161°$ (c, 1% in ethanol).

Anal.: Calc'd. for C$_{15}$H$_{17}$NO$_3$S 0.25 H$_2$O: C, 60.89; H, 5.96; N, 4.73; SH, 11.17, Found: C, 60.80; H, 5.92; N, 4.48; SH, 10.64.

EXAMPLE 5

[1(S)]-1-[3-(Acetylthio)-2-methyl-1-oxopropyl]-4-hydroxy-4-phenyl-L-proline (a) N-Carbobenzyloxy-4-hydroxy-4-phenyl-L-proline A stirred solution of N-carbobenzyloxy-4-keto-L-proline (13.2 g., 0.05 mole) in 400 ml. of tetrahydrofuran is maintained at 20°–25° while 65 ml. of 1.9N phenyl lithium in benzene-hexane (0.12 mole) is added over a period of ten minutes. The resulting turbid mixture is stirred overnight at room temperature, poured onto a solution of 14 g. of ammonia chloride in 140 ml. of ice-water, and acidified with 23 ml. of 6N hydrochloric acid. The organic phase is separated and the aqueous phase is extracted with 100 ml. of ethyl acetate. The organic phases are combined, dried (MgSO$_4$), filtered and the solvent evaporated to give 19.5 g. of a brown oil. This oil is treated with 100 ml. of ether and 70 ml. of N sodium hydroxide and stirred. The aqueous phase is separated and the ether layer is extracted twice with 100 ml. of water. The aqueous phases are combined, cooled, acidified with 6N hydrochloric acid, and the product is extracted three times with 50 ml. of ethyl acetate. The organic layers are combined, dried (MgSO$_4$), filtered and the solvent evaporated to give 12.5 g. of a foam-like solid. This material is dissolved in 400 ml. of ethyl acetate and treated with a solution of 5.6 g. of 1-adamantanamine in 100 ml. of ethyl acetate to give a heavy precipitate of the salt. After standing overnight at room temperature, the tan solid is filtered, washed with ethyl acetate and dried in a desiccator to yield 15.7 g. of a mixture of trans and cis isomers of the 1-adamantanamine salt of N-carbobenzyloxy-4-hydroxy-4-phenyl-L-proline; m.p. 205°–208° (red melt, s. 165°). Thin layer chromatography on silica gel using a mixture of methylene chloride, methanol, and acetic acid (8:1:1) shows the presence of the trans and cis isomers.

A suspension of 15 g. of the above 1-adamantanamine salt in 50 ml. of water and 10 ml. of ethyl acetate is stirred and acidified with 7 ml. of 6N hydrochloric acid. The mixture is shaken and the layers are separated. The aqueous phase is extracted twice with 50 ml. of ethyl acetate. The organic phases are combined, extracted three times with 10 ml. of water, dried (MgSO$_4$), filtered, and the solvent evaporated to give 10.3 g. of foam-like solid N-carbobenzyloxy-4-hydroxy-4-phenyl-L-proline.

(b) 4-Hydroxy-4-phenyl-L-proline

A soluion of the N-carbobenzyloxy-4-hydroxy-4-phenyl-L-proline from part (a) is treated with a 5% palladium carbon catalyst and hydrogenated according to the procedure of Example 1(b) to yield 4-hydroxy-4-phenyl-L-proline.

(c)

[1(S)]-1-[3-(Acetylthio)-2-methyl-1-oxopropyl]-4-hydroxy-4-phenyl-L-proline

The 4-hydroxy-4-phenyl-L-proline from part (b) is treated with D-3-acetylthio-2-methylpropionyl chloride according to the procedure of Example 1(c) to yield [1(S)]-1-[3-(acetylthio)-2-methyl-1-oxopropyl]-4-hydroxy-4-phenyl-L-proline.

EXAMPLE 6

[1(S)]-4-Hydroxy-1-(3-mercapto-2-methyl-1-oxopropyl)-4-phenyl-L-proline

The [1(S)]-1-[3-(acetylthio)-2-methyl-1-oxopropyl]-4-hydroxy-4-phenyl-L-proline from Example 5 is treated with concentrated ammonia according to the procedure of Example 2 to yield [1(S)]-4-hydroxy-1-(3-mercapto-2-methyl-1-oxopropyl)-4-phenyl-L-proline.

EXAMPLE 7

[1(S)]-4-Hydroxy-1-(3-mercapto-2-methyl-1-oxopropyl)-4-methyl-L-proline (a) N-Carbobenzyloxy-4-hydroxy-4-methyl-L-proline Following the procedure of Example 1(a) but substituting an equivalent amount of methyl magnesium bromide for the phenylmagnesium bromide one obtains N-carbobenzyloxy-4-hydroxy-4-methyl-L-proline.

(b) [1(S)]-1-[3-(Acetylthio)-2-methyl-1-oxopropyl]-4-hydroxy-4-methyl-L-proline

The N-carbobenzyloxy-4-hydroxy-4-methyl-L-proline from part (a) is hydrogenated according to the procedure of Example 1(b) to yield 4-hydroxy-4-methyl-L-proline. This amino acid is then reacted with D-3-acetylthio-2-methylpropionyl chloride according to the procedure of Example 1(c) to yield [1(S)]-1-[3-(acetylthio)-2-methyl-1-oxopropyl]-4-hydroxy-4-methyl-L-proline.

(c) [1(S)]-4-Hydroxy-1-(3-mercapto-2-methyl-1-oxopropyl)-4-methyl-L-proline

The product from part (b) is treated with concentrated ammonia according to the procedure of Example 2 to yield [1(S)]-4-hydroxy-1-(3-mercapto-2-methyl-1-oxopropyl)-4-methyl-L-proline.

EXAMPLE 8

[1(S),2S]-2,5-Dihydro-1-(3-mercapto-2-methyl-1-oxopropyl)-4-methyl-1H-pyrrole-2-carboxylic acid (a) 3,4-Dehydro-4-methyl-L-proline The N-carbobenzyloxy-4-hydroxy-4-methyl-L-proline from Example 7(a) is treated with hydrochloric acid according to the procedure of Example 3(a) to yield 3,4-dehydro-4-methyl-L-proline.

(b) [1(S),2S]-1-[3-(Acetylthio)-2-methyl-1-oxopropyl]-2,5-dihydro-4-methyl-1H-pyrrole-2-carboxylic acid The 3,4-dehydro-4-methyl-L-proline from part (a) is reacted with D-3-acetylthio-2-methylpropionyl chloride according to the procedure of Example 3(b) to yield [1(S),2S]-1-[3-(acetylthio)-2-methyl-1-oxopropyl]-2,5-dihydro-4-methyl-1H-pyrrole-2-carboxylic acid.

(c) [1(S),2S]-2,5-Dihydro-1-(3-mercapto-2-methyl-1-oxopropyl)-4-methyl-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-methyl-1H-pyrrole-2-carboxylic acid.

EXAMPLE 9

4-Ethyl-4-hydroxy-1-(3-mercapto-1-oxopropyl)-L-proline (a) N-Carbobenzyloxy-4-ethyl-4-hydroxy L-proline Following the procedure of Example 1(a) but substituting an equivalent amount of ethylmagnesium bromide for the phenylmagnesium bromide one obtains N-carbobenzyloxy-4-ethyl-4-hydroxy-L-proline.

(b) 1-[3-(Acetylthio)-1-oxopropyl]-4-ethyl-4-hydroxy-L-proline

The N-carbobenzyloxy-4-ethyl-4-hydroxy-L-proline from part (a) is hydrogenated according to the procedure of Example 1(b) to yield 4-ethyl-4-hydroxy-L-proline. This amino acid is then reacted with 3-acetylthiopropionyl chloride according to the procedure of Example 1(c) to yield 1-[3-(acetylthio)-1-oxopropyl]-4-ethyl-4-hydroxy-L-proline.

(c) 4-Ethyl-4-hydroxy-1-(3-mercapto-1-oxopropyl)-L-proline

The product from part (b) is treated with concentrated ammonia according to the procedure of Example 2 to yield 4-ethyl-4-hydroxy-1-(3-mercapto-1-oxopropyl)-L-proline.

EXAMPLE 10

(2S)-2,5-Dihydro-4-ethyl-1-(3-mercapto-1-oxopropyl)-1H-pyrrole-2-carboxylic acid (a) 3,4-Dehydro-4-ethyl-L-proline The N-carbobenzyloxy-4-ethyl-4-hydroxy-L-proline from Example 9(a) is treated with hydrochloric acid according to the procedure of Example 3(a) to yield 3,4-dehydro-4-ethyl-L-proline.

(b) (2S)-1-[3-(Acetylthio)-1-oxopropyl]-2,5-dihydro-4-ethyl-1H-pyrrole-2-carboxylic acid The 3,4-dehydro-4-ethyl-L-proline from part (a) is reacted with 3-acetylthiopropionyl chloride according to the procedure of Example 3 (b) to yield (2S)-1-[3-(acetylthio)-1-oxopropyl]-2,5-dihydro-4-ethyl-1H-pyrrole-2-carboxylic acid.

(c) (2S)-2,5-Dihydro-4-ethyl-1-(3-mercapto-1-oxopropyl)-1H-pyrrole-2-carboxylic acid The product from part (b) is treated with concentrated ammonia according to the procedure of Example 4 to yield (2S)-2,5-dihydro-4-ethyl-1-(3-mercapto-1-oxopropyl)-1H-pyrrole-2-carboxylic acid.

EXAMPLE 11

[1(S)]-4-Hydroxy-1-(3-mercapto-2-methyl-1-oxopropyl)-4-t-butyl-L-proline (a) N-Carbobenzyloxy-4-hydroxy-4-t-butyl-L-proline Following the procedure of Example 5 (a) but substituting an equivalent amount of t-butyl lithium for the phenyllithium one obtains N-carbobenzyloxy-4-hydroxy-4-t-butyl-L-proline.

(b) [1(S)]-1-[3-(Acetylthio)-2-methyl-1-oxopropyl]-4-hydroxy-4-t-butyl-L-proline The N-carbobenzyloxy-4-hydroxy-4-t-butyl-L-proline from part (a) is hydrogenated according to the procedure of Example 1 (b) to yield 4-hydroxy-4-t-butyl-L-proline. This amino acid is then reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-t-butyl-L-proline.

(c)
[1(S)]-4-Hydroxy-1-(3-mercapto-2-methyl-1-oxopropyl)-4-t-butyl-L-proline

The product from part (b) is treated with concentrated ammonia according to the procedure of Example 2 to yield [1(S)]-4-hydroxy-1-(3-mercapto-2-methyl-1-oxopropyl)-4-t-butyl-L-proline.

EXAMPLE 12

[1(S),2S]-2,5-Dihydro-1-(3-mercapto-2-methyl-1-oxopropyl)-4-t-butyl-1H-pyrrole-2-carboxylic acid (a) 3,4-Dehydro-4-t-butyl-L-proline The N-carbobenzyloxy-4-hydroxy-4-t-butyl-L-proline from Example 11 (a) is treated with hydrochloric acid according to the procedure of Example 3 (a) to yield 3,4-dehydro-4-t-butyl-L-proline.

(b)
[1(S),2S]-1-[3-(Acetylthio)-2-methyl-1-oxopropyl]-2,5-dihydro-4-t-butyl-1H-pyrrole-2-carboxylic acid The 3,4-dehydro-4-t-butyl-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-t-butyl-1H-pyrrole-2-carboxylic acid.

(c)
[1(S),2S]-2,5-Dihydro-1-(3-mercapto-2-methyl-1-oxopropyl)-4-t-butyl-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-t-butyl-1H-pyrrole-2-carboxylic acid.

EXAMPLE 13

4-Hydroxy-4-[(4-methyl)phenyl]-1-(4-mercapto-1-oxobutyl)-L-proline (a)
N-Carbobenzyloxy-4-hydroxy-4-[(4-methyl)phenyl]-L-proline Following the procedure of Example 1 (a) but substituting an equivalent amount of 4-methylphenyl magnesium bromide for the phenylmagnesium bromide one obtains N-carbobenzyloxy-4-hydroxy-4-[(4-methyl)phenyl]-L-proline.

(b)
1-[4-(Acetylthio)-1-oxobutyl]-4-hydroxy-4-[(4-methyl)phenyl]-L-proline

The N-carbobenzyloxy-4-hydroxy-4-[(4-methyl)phenyl]-L-proline form part (a) is hydrogenated according to the procedure of Example 1 (b) to yield 4-hydroxy-4-[(4-methyl)phenyl]-L-proline. This amino acid is then reacted with 4-acetylthiobutyroyl chloride according to the procedure of Example 1 (c) to yield 1-[4-(acetylthio)-1-oxobutyl]-4-hydroxy-4-[(4-methyl)phenyl]-L-proline.

(c)
4-Hydroxy-4-[(4-methyl)phenyl]-1-(4-mercapto-1-oxobutyl)-L-proline

The product from part (b) is treated with concentrated ammonia according to the procedure of Example 2 to yield 4-hydroxy-4-[(4-methyl)phenyl]-1-(4-mercapto-1-oxobutyl)-L-proline.

EXAMPLE 14

(2S)-2,5-Dihydro-4-[(4-methyl)phenyl]-1-(4-mercapto-1-oxobutyl)-1H-pyrrole-2-carboxylic acid (a) 3,4-Dehydro-4-[(4-methyl)phenyl]-L-proline The N-carbobenzyloxy-4-hydroxy-4-[(4-methyl)phenyl]-L-proline from Example 13 (a) is treated with hydrochloric acid according to the procedure of Example 3 (a) to yield 3,4-dehydro-4-[(4-methyl)phenyl]-L-proline.

(b)
(2S)-1-[4-(Acetylthio)-1-oxobutyl]-2,5-dihydro-4-[(4-methyl)phenyl]-1H-pyrrole-2-carboxylic acid The 3,4-dehydro-4-[(4-methyl)phenyl]-L-proline from part (a) is reacted with 4-acetylthiobutyroyl chloride according to the procedure of Example 3 (b) to yield (2S)-1-[4-(acetylthio)-1-oxobutyl]-2,5-dihydro-4-[(4-methyl)phenyl]-1H-pyrrole-2-carboxylic acid.

(c)
(2S)-2,5-Dihydro-4-[(4-methyl)phenyl]-1-(4-mercapto-1-oxobutyl)-1H-pyrrole-2-carboxylic acid The product from part (b) is treated with concentrated ammonia according to the procedure of Example 4 to yield (2S)-2,5-dihydro-4-[(4-methyl)phenyl]-1-(4-mercapto-1-oxobutyl)-1H-pyrrole-2-carboxylic acid.

EXAMPLE 15

4-Hydroxy-1-(2-mercapto-1-oxoethyl)-4-(phenylmethyl)-L-proline (a)
N-Carbobenzyloxy-4-hydroxy-4-(phenylmethyl)-L-proline Following the procedure of Example 1 (a) but substituting an equivalent amount of benzylmagnesium chloride for the phenylmagnesium bromide one obtains N-carbobenzyloxy-4-hydroxy-4-(phenylmethyl)-L-proline.

(b)
1-[2-(Acetylthio)-1-oxoethyl]-4-hydroxy-4-(phenylmethyl)-L-proline

The N-carbobenzyloxy-4-hydroxy-4-(phenylmethyl)-L-proline from part (a) is hydrogenated according to the procedure of Example 1 (b) to yield 4-hydroxy-4-(phenylmethyl)-L-proline. This amino acid is then reacted with 2-acetylthioacetyl chloride according to the procedure of Example 1 (c) to yield 1-[2-(acetylthio)-1-oxoethyl]-4-hydroxy-4-(phenylmethyl)-L-proline.

(c)
4-Hydroxy-1-(2-mercapto-1-oxoethyl)-4-(phenylmethyl)-L-proline

The product from part (b) is treated with concentrated ammonia according to the procedure of Example 2 to yield 4-hydroxy-1-(2-mercapto-1-oxoethyl)-4-(phenylmethyl)-L-proline.

EXAMPLE 16

(2S)-2,5-Dihydro-1-(2-mercapto-1-oxoethyl)-4-(phenylmethyl)-1H-pyrrole-2-carboxylic acid (a) 3,4-Dehydro-4-(phenylmethyl)-L-proline The N-carbobenzyloxy-4-hydroxy-4-(phenylmethyl)-L-proline from Example 15 (a) is treated with hydrochloric acid according to the procedure of Example 3 (a) to yield 3,4-dehydro-4-(phenylmethyl)-L-proline.

(b) (2S)-1-[2-(Acetylthio)-1-oxoethyl]-2,5-dihydro-4-(phenylmethyl)-1H-pyrrole-2-carboxylic acid The 3,4-dehydro-4-(phenylmethyl)-L-proline from part (a) is reacted with 2-acetylthioacetyl chloride according to the procedure of Example 3 (b) to yield (2S)-1-[2-(acetylthio)-1-oxoethyl]-2,5-dihydro-4-(phenylmethyl)-1H-pyrrole-2-carboxylic acid.

(c) (2S)-2,5-Dihydro-1-(2-mercapto-1-oxoethyl)-4-(phenylmethyl)-1H-pyrrole-2-carboxylic acid The product from part (b) is treated with concentrated ammonia according to the procedure of Example 4 to yield (2S)-2,5-dihydro-1-(2-mercapto-1-oxoethyl)-4-(phenylmethyl)-1H-pyrrole-2-carboxylic acid.

EXAMPLE 17

[1(S),4R]-1-[3-[[(4-Methoxy)phenylmethyl]thio]-2-trifluoromethyl-1-oxopropyl]-4-hydroxy-4-phenyl-L-proline (a) 3-[[(4-Methoxy)phenylmethyl]thio]-2-trifluoromethylpropionyl chloride A neat mixture of 1-trifluoromethylacrylic acid (3.9 g.) and 4-methoxybenzylthiol (4.3 g.) is stirred at 100°–110° for one hour. The mixture is allowed to cool to room temperature and the solid is recrystallized from cyclohexane to yield 3-[[(4-methoxy)phenylmethyl]thio]-2-trifluoromethylpropanoic acid; m.p. 72°–74°.

Treatment of this acid with thionyl chloride yields 3-[[(4-methoxy)phenylmethyl]thio]-2-trifluoromethylpropionyl chloride.

(b) [1(S),4R]-1-[3-[[(4-Methoxy)phenylmethyl]thio]-2-trifluoromethyl-1-oxopropyl]-4-hydroxy-4-phenyl-L-proline The 3-[[(4-methoxy)phenylmethyl]thio]-2-trifluoromethylpropionyl chloride from part (a) is reacted with cis-4-hydroxy-trans-4-phenyl-L-proline from Example 1 (b) to yield [1(S),4R]-1-[3-[[(4 methoxy)phenylmethyl]thio]-2-trifluoromethyl-1-oxopropyl]-4-hydroxy-4-phenyl-L-proline.

EXAMPLE 18

[1(S),4R]-4-Hydroxy-1-(3-mercapto-2-trifluoromethyl-1-oxopropyl)-4-phenyl-L-proline The [1(S),4R]-1-[3-[[(4-methoxy)phenylmethyl]thio]-2-trifluoromethyl-1-oxopropyl]-4-hydroxy-4-phenyl-L-proline from Example 17 is mixed with trifluoroacetic acid and anisole under nitrogen. The solvents are removed under vacuum to yield as a residue [1(S),4R]-4-hydroxy-1-(3-mercapto-2-trifluoromethyl-1-oxopropyl)-4-phenyl-L-proline.

EXAMPLE 19

[1(S),2S]-1-[3-[[(4-Methoxy)phenylmethyl]thio]-2-trifluoromethyl-1-oxopropyl]-2,5-dihydro-4-phenyl-1H-pyrrole-2-carboxylic acid The 3-[[(4-methoxy)phenylmethyl]thio]-2-trifluoromethylpropionyl chloride from Example 17 (a) is reacted with 3,4-dehydro-4-phenyl-L-proline from Example 3 (a) to yield [1(S),2S]-1-[3-[[(4-methoxy)phenylmethyl]thio]-2-trifluoromethyl-1-oxopropyl]-2,5-dihydro-4-phenyl-1H-pyrrole-2-carboxylic acid.

EXAMPLE 20

[1(S),2S]-2,5-Dihydro-1-(3-mercapto-2-trifluoromethyl-1-oxopropyl)-4-phenyl-1H-pyrrole-2-carboxylic acid The [1(S),2S]-1-[3-[[(4-methoxy)phenylmethyl]thio]-2-trifluoromethyl-1-oxopropyl]-2,5-dihydro-4-phenyl-1H-pyrrole-2-carboxylic acid from Example 19 is mixed with trifluoroacetic acid and anisole and stirred under nitrogen. The solvents are removed under vacuum to yield as a residue [1(S),2S]-2,5-dihydro-1-(3-mercapto-2-trifluoromethyl-1-oxopropyl)-4-phenyl-1H-pyrrole-2-carboxylic acid.

EXAMPLE 21

[1(S),4R]-1-[3-[[(4-Methoxy)phenylmethyl]thio]-2-methylthio-1-oxopropyl]-4-hydroxy-4-phenyl-L-proline (a) 3-[[(4-Methoxy)phenylmethyl]thio]-2-methylthiopropionyl chloride 3-[[(4-Methoxy)phenylmethyl]thio]-2-methylthiopropanoic acid prepared according to the procedure of Example 10 in U.S. Pat. No. 4,116,962 is treated with thionyl chloride to yield 3-[[(4-methoxy)phenylmethyl]thio]-2-methylthiopropionyl chloride.

(b) [1(S),4R]-1-[3-[[(4-Methoxy)phenylmethyl]thio]-2-methylthio-1-oxopropyl]-4-hydroxy-4-phenyl-L-proline The 3-[[(4-methoxy)phenylmethyl]thio]-2-methylthiopropionyl chloride from part (a) is reacted with cis-4-hydroxy-trans-4-phenyl-L-proline from Example 1 (b) to yield [1(S),4R]-1-[3-[[(4-methoxy)phenylmethyl]thio]-2-methylthio-1-oxopropyl]-4-hydroxy-4-phenyl-L-proline.

EXAMPLE 22

[1(S),4R]-4-Hydroxy-1-(3-mercapto-2-methylthio-1-oxopropyl)-4-phenyl-L-proline

The [1(S),4R]-1-[3-[[(4-methoxy)phenylmethyl]thio]-2-methylthio-1-oxopropyl]-4-hydroxy-4-phenyl-L-proline from Example 21 is mixed with trifluoroacetic acid and anisole under nitrogen. The solvents are removed under vacuum to yield as a residue [1(S),4R]-4-hydroxy-1-(3-mercapto-2-methylthio-1-oxopropyl)-4-phenyl-L-proline.

EXAMPLE 23

[1(S),2S]-1-[3-[[(4-Methoxy)phenylmethyl]thio]-2-methylthio-1-oxopropyl]-2,5-dihydro-4-phenyl-1H-pyrrole-2-carboxylic acid The 3-[[(4-methoxy)phenylmethyl]thio]-2-methylthiopropionyl chloride from Example 21 (a) is reacted with 3,4-dehydro-4-phenyl-L-proline from Example 3 (a) to yield [1(S),2S]-1-[3-[[(4-methoxy)phenylmethyl]-thio]-2-methylthio-1-oxopropyl]-2,5-dihydro-4-phenyl-1H-pyrrole-2-carboxylic acid.

EXAMPLE 24

[1(S),2S]-2,5-Dihydro-1-(3-mercapto-2-methylthio-1-oxopropyl)-4-phenyl-1H-pyrrole-2-carboxylic acid The [1(S),2S]-1-[3-[[(4-methoxy)phenylmethyl]thio]-2-methylthio-1-oxopropyl]-2,5-dihydro-4-phenyl-1H-pyrrole-2-carboxylic acid from Example 23 is mixed with trifluoroacetic acid and anisole and stirred under nitrogen. The solvents are removed under vacuum to yield as a residue [1(S),2S]-2,5-dihydro-1-(3-mercapto-2-methylthio-1-oxopropyl)-4-phenyl-1H-pyrrole-2-carboxylic acid.

EXAMPLE 25

[1(S)]-4-Hydroxy-1-(3-mercapto-2-methyl-1-oxopropyl)-4-(3-fluorophenyl)-L-proline (a) N-Carbobenzyloxy-4-hydroxy-4-(3-fluorophenyl)-L-proline Following the procedure of Example 1 (a) but substituting an equivalent amount of 3-fluorophenyl-magnesium bromide for the phenylmagnesium bromide one obtains N-carbobenzyloxy-4-hydroxy-4-(3-fluorophenyl)-L-proline.

(b) [1(S)]-1-[3-(Acetylthio)-2-methyl-1-oxopropyl]-4-hydroxy-4-(3-fluorophenyl)-L-proline The N-carbobenzyloxy-4-hydroxy-4-(3-fluorophenyl)-L-proline from part (a) is hydrogenated according to the procedure of Example 1 (b) to yield 4-hydroxy-4-(3-fluorophenyl)-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-(3-fluorophenyl)-L-proline.

(c) [1(S)]-4-Hydroxy-1-(3-mercapto-2-methyl-1-oxopropyl)-4-(3-fluorophenyl)-L-proline The product from part (b) is treated with concentrated ammonia according to the procedure of Example 2 to yield [1(S)]-4-hydroxy-1-(3-mercapto-2-methyl-1-oxopropyl)-4-(3-fluorophenyl)-L-proline.

EXAMPLE 26

[1(S),2S]-2,5-Dihydro-1-(3-mercapto-2-methyl-1-oxopropyl)-4-(3-fluorophenyl)-1H-pyrrole-2-carboxylic acid (a) 3,4-Dehydro-4-(3-fluorophenyl)-L-proline The N-carbobenzyloxy-4-hydroxy-4-(3-fluorophenyl)-L-proline from Example 25 (a) is treated with hydrochloric acid according to the procedure of Example 3 (a) to yield 3,4-dehydro-4-(3-fluorophenyl)-L-proline.

(b) [1(S),2S]-1-[3-(Acetylthio)-2-methyl-1-oxopropyl]-2,5-dihydro-4-(3-fluorophenyl)-1H-pyrrole-2-carboxylic acid The 3,4-dehydro-4-(3-fluorophenyl)-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-(3-fluorophenyl)-1H-pyrrole-2-carboxylic acid.

(c) [1(S),2S]-2,5-Dihydro-1-(3-mercapto-2-methyl-1-oxopropyl)-4-(3-fluorophenyl)-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-(3-fluorophenyl)-1H-pyrrole-2-carboxylic acid.

EXAMPLE 27

[1(S)]-4-Hydroxy-1-(3-mercapto-2-methyl-1-oxopropyl)-4-(4-chlorophenylethyl)-L-proline (a) N-Carbobenzyloxy-4-hydroxy-4-(4-chlorophenylethyl)-L-proline Following the procedure of Example 1 (a) but substituting an equivalent amount of 4-chlorophenylethyl magnesium bromide for the phenylmagnesium bromide one obtains N-carbobenzyloxy-4-hydroxy-4-(4-chlorophenylethyl)-L-proline.

(b) [1(S)]-1-[3-(Acetylthio)-2-methyl-1-oxopropyl]-4-hydroxy-4-(4-chlorophenylethyl)-L-proline The N-carbobenzyloxy-4-hydroxy-4-(4-chlorophenylethyl)-L-proline from part (a) is hydrogenated according to the procedure of Example 1 (b) to yield 4-hydroxy-4-(4-chlorophenylethyl)-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-(4-chlorophenylethyl)-L-proline.

(c) [1(S)]-4-Hydroxy-1-(3-mercapto-2-methyl-1-oxopropyl)-4-(4-chlorophenylethyl)-L-proline The product from part (b) is treated with concentrated ammonia according to the procedure of Example 2 to yield [1(S)]-4-hydroxy-1-(3-mercapto-2-methyl-1-oxopropyl)-4-(4-chlorophenylethyl)-L-proline.

EXAMPLE 28

[1(S),2S]-2,5-Dihydro-1-(3-mercapto-2-methyl-1-oxopropyl)-4-(4-chlorophenylethyl)-1H-pyrrole-2-carboxylic acid (a) 3,4-Dehydro-4-(4-chlorophenylethyl)-L-proline The N-carbobenzyloxy-4-hydroxy-4-(4-chlorophenylethyl)-L-proline from Example 27 (a) is treated with hydrochloric acid according to the procedure of Example 3 (a) to yield 3,4-dehydro-4-(4-chlorophenylethyl)-L-proline.

(b) [1(S),2S]-1-[3-(Acetylthio)-2-methyl-1-oxopropyl]-2,5-dihydro-4-(4-chlorophenylethyl)-1H-pyrrole-2-carboxylic acid The 3,4-dehydro-4-(4-chlorophenylethyl)-L-proline from part (a) is reacted with D-3-acetylthio-2-methylpropionyl chloride according to the procedure of Example 3 (b) to yield [1(S),2S]-1-[3-(acetylthio)-2-methyl- 1-oxopropyl]-2,5-dihydro-4-(4-chlorophenylethyl)-1H-pyrrole-2-carboxylic acid.

(c)
[1(S),2S]-2,5-Dihydro-1-(3-mercapto-2-methyl-1-oxopropyl)-4-(4-chlorophenylethyl)-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-(4-chlorophenylethyl)-1H-pyrrole-2-carboxylic acid.

EXAMPLE 29

4-Hydroxy-1-(3-mercapto-1-oxopropyl)-4-[(4-trifluoromethyl)phenyl]-L-proline (a)
N-Carbobenzyloxy-4-hydroxy-4-[(4-trifluoromethyl)phenyl]-L-proline Following the procedure of Example 1 (a) but substituting an equivalent amount of [(4-trifluoromethyl)phenyl]magnesium bromide for the phenylmagnesium bromide one obtains N-carbobenzyloxy-4-hydroxy-4-[(4-trifluoromethyl)phenyl]-L-proline.

(b)
1-[(3-Acetylthio)-1-oxopropyl]-4-hydroxy-4-[(4-trifluoromethyl)phenyl]-L-proline The N-carbobenzyloxy-4-hydroxy-4-[(4-trifluoromethyl)phenyl]-L-proline from part (a) is hydrogenated according to the procedure of Example 1 (b) to yield 4-hydroxy-4-[(4-trifluoromethyl)phenyl]-L-proline. This amino acid is reacted with 3-acetylthiopropionyl chloride according to the procedure of Example 1 (c) to yield 1-[3-(acetylthio)-1-oxopropyl]-4-hydroxy-4-[(4-trifluoromethyl)phenyl]-L-proline.

(c)
4-Hydroxy-1-(3-mercapto-1-oxopropyl)-4-[(4-trifluoromethyl)phenyl]-L-proline The product from part (b) is treated with concentrated ammonia according to the procedure of Example 2 to yield 4-hydroxy-1-(3-mercapto-1-oxopropyl)-4-[(4-trifluoromethyl)phenyl]-L-proline.

EXAMPLE 30

(2S)-2,5-Dihydro-1-(3-mercapto-1-oxopropyl)-4-[(4-trifluoromethyl)phenyl]-1H-pyrrole-2-carboxylic acid (a)
3,4-Dehydro-4-[(4-trifluoromethyl)phenyl]-L-proline The N-carbobenzyloxy-4-hydroxy-4-[(4-trifluoromethyl)phenyl]-L-proline from Example 29 (a) is treated with hydrochloric acid according to the procedure of Example 3 (a) to yield 3,4-dehydro-4-[(4-trifluoromethyl)phenyl]-L-proline.

(b)
(2S)-1-[3-(Acetylthio)-1-oxopropyl]-2,5-dihydro-4-[(4-trifluoromethyl)phenyl]-1H-pyrrole-2-carboxylic acid The 3,4-dihydro-4-[(4-trifluoromethyl)phenyl]-L-proline from part (a) is reacted with 3-acetylthiopropionyl chloride according to the procedure of Example 3 (b) to yield (2S)-1-[3-(acetylthio)-1-oxopropyl]-2,5-dihydro-4-[(4-trifluoromethyl)phenyl]-1H-pyrrole-2-carboxylic acid.

(c)
(2S)-2,5-Dihydro-1-(3-mercapto-1-oxopropyl)-4-[(4-trifluoromethyl)phenyl]-1H-pyrrole-2-carboxylic acid The product from part (b) is treated with concentrated ammonia according to the procedure of Example 4 to yield (2S)-2,5-dihydro-1-(3-mercapto-1-oxopropyl)-4-[(4-trifluoromethyl)phenyl]-1H-pyrrole-2-carboxylic acid.

EXAMPLE 31

[1(S)]-4-Hydroxy-1-(3-mercapto-2-trifluoromethyl-1-oxopropyl)-4-(2-methoxyphenyl)-L-proline (a)
N-Carbobenzyloxy-4-hydroxy-4-(2-methoxyphenyl)-L-proline Following the procedure of Example 1 (a) but substituting an equivalent amount of (2-methoxyphenyl) magnesium bromide for the phenylmagnesium bromide one obtains N-carbobenzyloxy-4-hydroxy-4-(2-methoxyphenyl)-L-proline.

(b)
[1(S)]-1-[3-[[(4-Methoxy)phenylmethyl]thio]-2-trifluoromethyl-1-oxopropyl]-4-hydroxy-4-(2-methoxyphenyl)-L-proline The N-carbobenzyloxy-4-hydroxy-4-(2-methoxyphenyl)-L-proline from part (a) is hydrogenated according to the procedure of Example 1 (b) to yield 4-hydroxy-4-(2-methoxyphenyl)-L-proline. This amino acid is reacted with 3-[[(4-methoxy)phenylmethyl]thio]-2-trifluoromethylpropionyl chloride from Example 17 (a) to yield [1(S)]-1-[3-[[(4-methoxy)phenylmethyl]thio]-2-trifluoromethyl-1-oxopropyl]-4-hydroxy-4-(2-methoxyphenyl)-L-proline.

(c)
[1(S)]-4-Hydroxy-1-(3-mercapto-2-trifluoromethyl-1-oxopropyl)-4-(2-methoxyphenyl)-L-proline The product from part (b) is treated with trifluoroacetic acid and anisole according to the procedure of Example 18 to yield [1(S)]-4-hydroxy-1-(3-mercapto-2-trifluoromethyl-1-oxopropyl)-4-(2-methoxyphenyl)-L-proline.

EXAMPLE 32

[1(S),2S]-2,5-Dihydro-1-(3-mercapto-2-trifluoromethyl-1-oxopropyl)-4-(2-hydroxyphenyl)-1H-pyrrole-2-carboxylic acid (a) 3,4-Dehydro-4-(2-methoxyphenyl)-L-proline The N-carbobenzyloxy-4-hydroxy-4-(2-methoxyphenyl)-L-proline from Example 31 (a) is treated with hydrochloric acid according to the procedure of Example 3 (a) to yield 3,4-dehydro-4-(2-methoxyphenyl)-L-proline.

(b) [1(S), 2S]-1-[3-[[(4-Methoxy)phenylmethyl]thio]-2-trifluoromethyl-1-oxopropyl]-2,5-dihydro-4-(2-methoxyphenyl)-1H-pyrrole-2-carboxylic acid The 3,4-dehydro-4-(2-methoxyphenyl)-L-proline from part (a) is reacted with 3-[[(4-methoxy)-phenylmethyl]thio]-2-trifluoromethylpropionyl chloride from Example 17 (a) to yield [1(S), 2S]-1-[3-[[(4-methoxy)-phenylmethyl]thio]-2-trifluoromethyl-1-oxopropyl]-

2,5-dihydro-4-(2-methoxyphenyl)-1H-pyrrole-2-carboxylic acid.

(c)

[1(S),2S]-2,5-Dihydro-1-(3-mercapto-2-trifluoromethyl-1-oxopropyl)-4-(2-hydroxyphenyl)-1H-pyrrole-2-carboxylic acid The product from part (b) is treated with trifluoroacetic acid and anisole according to the procedure of Example 20 to yield [1(S), 2S]-2,5-dihydro-1-(3-mercapto-2-trifluoromethyl-1-oxopropyl)-4-(2-methoxyphenyl)-1H-pyrrole-2-carboxylic acid. The latter is treated with pyridine hydrochloride for one hour at 100° to give [1(S),2S]-2,5-dihydro-1-(3-mercapto-2-trifluoromethyl-1-oxopropyl)-4-(2-hydroxyphenyl)-1H-pyrrole-2-carboxylic acid.

EXAMPLE 33

[1(S)]-4-Hydroxy-1-(3-mercapto-2-methyl-1-oxopropyl)-4-[(4-methylthio)phenylmethyl]-L-proline (a)

N-Carbobenzyloxy-4-hydroxy-4-[(4-methylthio)phenylmethyl]-L-proline

Following the procedure of Example 1 (a) but substituting an equivalent amount of 4-methylthiobenzyl magnesium bromide for the phenylmagnesium bromide one obtains N-carbobenzyloxy-4-hydroxy-4-[(4-methylthio)phenylmethyl]-L-proline.

(b)

[1(S)]-1-[3-(Acetylthio)-2-methyl-1-oxopropyl]-4-hydroxy-4-[(4-methylthio)phenylmethyl]-L-proline The N-carbobenzyloxy-4-hydroxy-4-[(4-methylthio)phenylmethyl]-L-proline from part (a) is hydrogenated according to the procedure of Example 1 (b) to yield 4-hydroxy-4-[(4-methylthio)phenylmethyl]-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-[(4-methylthio)phenylmethyl]-L-proline.

(c)

[1(S)]-4-Hydroxy-1-(3-mercapto-2-methyl-1-oxopropyl)-4-[(4-methylthio)phenylmethyl]-L-proline The product from part (b) is treated with concentrated ammonia according to the procedure of Example 2 to yield [1(S)]-4-hydroxy-1-(3-mercapto-2-methyl-1-oxopropyl)-4-[(4-methylthio)phenylmethyl]-L-proline.

EXAMPLE 34

[1(S),2S]-2,5-Dihydro-1-(3-mercapto-2-methyl-1-oxopropyl)-4-[(4-methylthio)phenylmethyl]-1H-pyrrole-2-carboxylic acid (a)

3,4-Dehydro-4-[(4-methylthio)phenylmethyl]-L-proline

The N-carbobenzyloxy-4-hydroxy-4-[(4-methylthio)phenylmethyl]-L-proline from Example 33 (a) is treated with hydrochloric acid according to the procedure of Example 3 (a) to yield 3,4-dehydro-4-[(4-methylthio)phenylmethyl]-L-proline.

(b)

[1(S),2S]-1-[3-(Acetylthio)-2-methyl-1-oxopropyl]-2,5-dihydro-4-[(4-methylthio)phenylmethyl]-1H-pyrrole-2-carboxylic acid The 3,4-dehydro-4-[(4-methylthio)phenylmethyl]-L-proline from part (a) is reacted with D-3-acetylthio-2-methylpropionyl chloride according to the procedure of Example 3 (b) to yield [1(S), 2S]-1-[3-(acetylthio)-2-methyl-1-oxopropyl]-2,5-dihydro-4-[(4-methylthio)phenylmethyl]-1H-pyrrole-2-carboxylic acid.

(c)

[1(S),2S]-2,5-Dihydro-1-(3-mercapto-2-methyl-1-oxopropyl-4-[(4-methylthio)phenylmethyl]-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-[(4-methylthio)-phenylmethyl]-1H-pyrrole-2-carboxylic acid.

EXAMPLE 35

[1(S)]-4-Hydroxy-1-(3-mercapto-2-methyl-1-oxopropyl)-4-(2-thienyl)-L-proline (a)

N-Carbobenzyloxy-4-hydroxy-4-(2-thienyl)-L-proline

Following the procedure of Example 1 (a) but substituting an equivalent amount of (2-thienyl) magnesium bromide for the phenylmagnesium bromide one obtains N-carbobenzyloxy-4-hydroxy 4-(2-thienyl)-L-proline.

(b)

[1(S)]-1-[3-(Acetylthio)-2-methyl-1-oxopropyl]-4-hydroxy-4-(2-thienyl)-L-proline The N-carbobenzyloxy-4-hydroxy-4-(2-thienyl)-L-proline from part (a) is hydrogenated according to the procedure of Example 1 (b) to yield trans-4-hydroxy-4-(2-thienyl)-L-proline. This amino acid is reacted with D-acetylthio-2-methylpropionyl chloride according to the procedure of Example 1 (c) to yield [1(S)]-1-[3-(acetylthio)-2-methyl-1-oxopropyl]-4-hydroxy-4-(2-thienyl)-L-proline.

(c)

[1(S)]-4-Hydroxy-1-(3-mercapto-2-methyl-1-oxopropyl)-4-(2-thienyl)-L-proline

The product from part (b) is treated with concentrated ammonia according to the procedure of Example 2 to yield [1(S)]-4-hydroxy-1-(3-mercapto-2-methyl-1-oxopropyl)-4-(2-thienyl)-L-proline.

EXAMPLE 36

[1(S),2S]-2,5-Dihydro-1-(3-mercapto-2-methyl-1-oxopropyl)-4-(2-thienyl)-1H-pyrrole-2-carboxylic acid (a) 3,4-Dehydro-4-(2-thienyl)-L-proline The N-carbobenzyloxy-4-hydroxy-4-(2-thienyl)-L-proline from Example 35 (a) is treated with hydrochloric acid according to the procedure of Example 3 (a) to yield 3,4-dehydro-4-(2-thienyl)-L-proline.

(b)

[1(S),2S]-1-[3-(Acetylthio)-2-methyl-1-oxopropyl]-2,5-dihydro-4-(2-thienyl)-1H-pyrrole-2-carboxylic acid The 3,4-dehydro-4-(2-thienyl)-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-(2-thienyl)-1H-pyrrole-2-carboxylic acid.

(c)

[1(S),2S]-2,5-Dihydro-1-(3-mercapto-2-methyl-1-oxopropyl)-4-(2-thienyl)-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-(2-thienyl)-1H-pyrrole-2-carboxylic acid.

EXAMPLE 37

4-Hydroxy-1-(3-Mercapto-1-oxopropyl)-4-[(2-thienyl)-methyl]-L-proline (a)

N-Carbobenzyloxy-4-hydroxy-4-[(2-thienyl)methyl]-L-proline

Following the procedure of Example 1 (a) but substituting an equivalent amount of [(2-thienyl)methyl]magnesium bromide for the phenylmagnesium bromide one obtains N-carbobenzyloxy-4-hydroxy-4-[(2-thienyl)methyl]-L-proline.

(b)

1-[3-(Acetylthio)-1-oxopropyl]-4-hydroxy-4-[(2-thienyl)methyl]-L-proline

The N-carbobenzyloxy-4-hydroxy-4-[(2-thienyl)methyl]-L-proline from part (a) is hydrogenated according to the procedure of Example 1 (b) to yield 4-hydroxy-4-[(2-thienyl)methyl]-L-proline. This amino acid is then reacted with 3-acetylthiopropionyl chloride according to the procedure of Example 1 (c) to yield 1-[3-(acetylthio)-1-oxopropyl]-4-hydroxy-4-[(2-thienyl)methyl]-L-proline.

(c)

4-Hydroxy-1-(3-mercapto-1-oxopropyl)-4-[(2-thienyl)-methyl]-L -proline

The product from part (b) is treated with concentrated ammonia according to the procedure of Example 2 to yield 4-hydroxy-1-(3-mercapto-1-oxopropyl)-4-[(2-thienyl)methyl]-L-proline.

EXAMPLE 38

(2S)-2,5-Dihydro-1-(3-mercapto-1-oxopropyl)-4-[(2-thienyl)methyl]-1H-pyrrole-2-carboxylic acid (a) 3,4-Dehydro-[(2-thienyl)methyl]-L-proline The N-carbobenzyloxy-4-hydroxy-4-[(2-thienyl)methyl]-L-proline from Example 37(a) is treated with hydrochloric acid according to the procedure of Example 3 (a) to yield 3,4-dehydro-4-[(2-thienyl)methyl]-L-proline.

(b)

(2S)-1-[3-(Acetylthio)-1-oxopropyl]-2,5-dihydro-4-[(2-thienyl)methyl]-1H-pyrrole-2-carboxylic acid The 3,4-dehydro-4-[(2-thienyl)methyl]-L-proline from part (a) is reacted with 3-acetylthiopropionyl chloride according to the procedure of Example 3 (b) to yield (2S)-1-[3-(acetylthio)-1-oxopropyl]-2,5-dihydro-4-[(2-thienyl)methyl]-L-pyrrole-2-carboxylic acid.

(c)

(2S)-2,5-Dihydro-1-(3-mercapto-1-oxopropyl)-4-[(2-thienyl)methyl]-1H-pyrrole-2-carboxylic acid The product from part (b) is treated with concentrated ammonia according to the procedure of Example 4 to yield (2S)-2,5-dihydro-1-(3-mercapto-1-oxopropyl)-4-[(2-thienyl)methyl]-1H-pyrrole-2-carboxylic acid.

EXAMPLE 39

[1(S)]-4-Hydroxy-1-(3-mercapto-2-trifluoromethyl-1-oxopropyl)-4-(3-thienyl)-L-proline (a)

N-Carbobenzyloxy-4-hydroxy-4-(3-thienyl)-L-proline

Following the procedure of Example 1 (a) but substituting an equivalent amount of (3-thienyl) magnesium bromide for the phenylmagnesium bromide one obtains N-carbobenzyloxy-4-hydroxy-4-(3-thienyl)-L-proline.

(b)

[1(S)]-1-[3-[[(4-Methoxy)phenylmethyl]thio]-2-trifluoromethyl-1-oxopropyl]-4-hydroxy-4-(3-thienyl)-L-proline The N-carbobenzyloxy-4-hydroxy-4-(3-thienyl)-L-proline from part (a) is hydrogenated according to the procedure of Example 1 (b) to yield 4-hydroxy-4-(3-thienyl)-L-proline. This amino acid is reacted with 3-[[(4-methoxy)phenylmethyl]-thio]-2-trifluoromethyl-propionyl chloride from Example 17 (a) to yield [1(S)]-1-[3-[[(4-methoxy)-phenylmethyl]thio]-2-trifluoromethyl-1-oxopropyl]-4-hydroxy-4-(3-thienyl)-L-proline.

(c)

[1(S)]-4-Hydroxy-1-(3-mercapto-2-trifluoro-methyl-1-oxopropyl)-4-(3-thienyl)-L-proline The product from part (b) is treated with trifluoroacetic acid and anisole according to the procedure of Example 18 to yield [1(S)]-4-hydroxy-1-(3-mercapto-2-trifluoromethyl-1-oxopropyl)-4-(3-thienyl)-L-proline.

EXAMPLE 40

[1(S),2S]-2,5-Dihydro-1-(3-mercapto-2-trifluoromethyl-1-oxopropyl)-4-(3-thienyl)-1H-pyrrole-2-carboxylic acid (a) 3,4-Dehydro-4-(3-thienyl)-L-proline The N-carbobenzyloxy-4-hydroxy-4-(3-thienyl)-L-proline from Example 39 (a) is treated with hydrochloric acid according to the procedure of Example 3 (a) to yield 3,4-dehydro-4-(3-thienyl)-L-proline.

(b)

[1(S),2S]-2,5-Dihydro-1-[3-[[(4-methoxy)phenylmethyl]thio]-2-trifluoromethyl-1-oxopropyl]-4-(3-thienyl)-1H-pyrrole-2-carboxylic acid The 3,4-dehydro-4-(3-thienyl)-L-proline from part (a) is reacted with 3-[[(4-methoxy)phenylmethyl]-thio]-2-trifluoromethylpropionyl chloride from Example 17 (a) to yield [1(S),2S]-2,5-dihydro-1-[3-[[(4-methoxy)-phenylmethyl]thio]-2-trifluoromethyl-1-oxopropyl]-4-(3-thienyl)-1H-pyrrole-2-carboxylic acid.

(c)
[1(S),2S]-2,5-Dihydro-1-(3-mercapto-2-trifluoromethyl-1-oxopropyl)-4-(3-thienyl)-1H-pyrrole-2-carboxylic acid The product from part (b) is treated with trifluoroacetic acid and anisole according to the procedure of Example 20 to yield [1(S),2S]-2,5-dihydro-1-(3-mercapto-2-trifluoromethyl-1-oxopropyl)-4-(3-thienyl)-1H-pyrrole-2-carboxylic acid.

EXAMPLE 41

[1(S)]-4-(2-Furyl)-4-hydroxy-1-(3-mercapto-2-ethyl-1-oxopropyl)-L-proline (a) N-Carbobenzyloxy-4-(2-furyl)-4-hydroxy-L-proline Following the procedure of Example 1 (a) but substituting an equivalent amount of (2-furyl) magnesium bromide for the phenylmagnesium bromide one obtains N-carbobenzyloxy-4-(2-furyl)-4-hydroxy-L-proline.

(b)
[1(S)]-1-[3-(Acetylthio)-2-ethyl-1-oxopropyl]-4-(2-furyl)-4-hydroxy-L-proline The N-carbobenzyloxy-4-(2-furyl)-4-hydroxy-L-proline from part (a) is hydrogenated according to the procedure of Example 1 (b) to yield 4-(2-furyl)-4-hydroxy-L-proline. This amino acid is reacted with D-3-acetylthio-2-ethylpropionyl chloride according to the procedure of Example 1 (c) to yield [1(S)]-1-(3-(acetylthio)-2-ethyl-1-oxopropyl]-4-(2-furyl)-4-hydroxy-L-proline.

(c)
[1(S)]-4-(2-Furyl)-4-hydroxy-1-(3-mercapto-2-ethyl-1-oxopropyl)-L-proline

The product from part (b) is treated with concentrated ammonia according to the procedure of Example 2 to yield [1(S)]-4-(2-Furyl)-4-hydroxy-1-(3-mercapto-2-ethyl-1-oxopropyl)-L-proline.

EXAMPLE 42

[1(S),2S]-2,5-Dihydro-4-(2-furyl)-1-(3-mercapto-2-ethyl-1-oxopropyl)-1H-pyrrole-2-carboxylic acid (a) 3,4-Dehydro-4-(2-furyl)-L-proline The N-carbobenzyloxy-4-hydroxy-4-(2-furyl)-L-proline from Example 41 (a) is treated with hydrochloric acid according to the procedure of Example 3 (a) to yield 3,4-dehydro-4-(2-furyl)-L-proline.

(b)
[1(S),2S]-1-[3-(Acetylthio)-2-ethyl-1-oxopropyl]-2,5-dihydro-4-(2-furyl)-1H-pyrrole-2-carboxylic acid The 3,4-dehydro-4-(2-furyl)-L-proline from part (a) is reacted with D-3-acetylthio-2-ethylpropionyl chloride to yield [1(S),2S]-1-[3-(acetylthio)-2-ethyl-1-oxopropyl]-4-(2-furyl)-1H-pyrrole-2-carboxylic acid.

(c)
[1(S),2S]-2,5-Dihydro-4-(2-furyl)-1-(3-mercapto-2-ethyl-1-oxopropyl)-1H-pyrrole-2-carboxylic acid The product from part (b) is treated with concentrated ammonia according to the procedure of Example 4 to yield [1(S),2S]-2,5-dihydro-4-(2-furyl)-1-(3-mercapto-2-ethyl-1-oxopropyl)-1H-pyrrole-2-carboxylic acid.

EXAMPLE 43

4-[(2-Furyl)methyl]-4-Hydroxy-1-(2-mercapto-1-oxoethyl)-L-proline (a)
N-Carbobenzyloxy-4-[(2-furyl)methyl]-4-hydroxy-L-proline Following the procedure of Example 1 (a) but substituting an equivalent amount of [(2-furyl)methyl]magnesium bromide for the phenylmagnesium bromide one obtains N-carbobenzyloxy-4-[(2-furyl)-methyl]-4-hydroxy-L-proline.

(b)
1-[2-(Acetylthio)-1-oxoethyl]-4-[(2-furyl)-methyl]-4-hydroxy-L-proline

The N-carbobenzyloxy-4-[(2-furyl)methyl]-4-hydroxy-L-proline from part (a) is hydrogenated according to the procedure of Example 1 (b) to yield 4-[(2-furyl)methyl]-4-hydroxy-L-proline. This amino acid is reacted with 2-acetylthioacetyl chloride according to the procedure of Example 1 (c) to yield 1-[2-(acetylthio)-1-oxoethyl]-4-[(2-furyl)methyl]-4-hydroxy-L-proline.

(c)
4-[(2-Furyl)methyl]-4-hydroxy-1-(2-mercapto-1-oxoethyl)-L-proline

The product from part (b) is treated with concentrated ammonia according to the procedure of Example 2 to yield 4-[(2-furyl)methyl]-4-hydroxy-1-(2-mercapto-1-oxoethyl)-L-proline.

EXAMPLE 44

(2S)-4-[(2-Furyl)methyl]-2,5-dihydro-1-(2-mercapto-1-oxoethyl)-1H-pyrrole-2-carboxylic acid (a) 4-[(2-Furyl)methyl]-3,4-dehydro-L-proline The N-carbobenzyloxy-4-[(2-furyl)methyl]-4-hydroxy-L-proline from Example 43 (a) is treated with hydrochloric acid according to the procedure of Example 3 (a) to yield 4-[(2-furyl)methyl]-3,4-dehydro-L-proline.

(b)
(2S)-1-[2-(Acetylthio)-1-oxoethyl-[(2-furyl)-methyl]-2,5-dihydro-1H-pyrrole-2-carboxylic acid 4-[(2-Furyl)methyl]-3,4-dehydro-L-proline from part (a) is reacted with 2-acetylthioacetyl chloride according to the procedure of Example 3 (b) to yield (2S)-1-[2-(acetylthio)-1-oxoethyl]-4-[(2-furyl)methyl]-2,5-dihydro-1H-pyrrole-2-carboxylic acid.

(c)
(2S)-4-[(2-Furyl)methyl]-2,5-dihyro-1-(2-mercapto-1-oxoethyl)-1H-pyrrole-2-carboxylic acid The product from part (b) is treated with concentrated ammonia according to the procedure of Example 4 to yield (2S)-4-[(2-furyl)methyl]-2,5-dihydro-1-(2-mercapto-1-oxoethyl)-1H-pyrrole-2-carboxylic acid.

EXAMPLE 45

[1(S)]-4-Hydroxy-1-(3-mercapto-2-methyl-1-oxopropyl)-4-[(4-pyridyl)methyl]-L-proline (a) N-Carbobenzyloxy-4-hydroxy-4-[(4-pyridyl)methyl]-L-proline Following the procedure of Example 5 (a) but substituting an equivalent amount of [(4-pyridyl)methyl]lithium for the phenyllithium one obtains N-carbobenzyloxy-4-hydroxy-4-[(4-pyridyl)methyl]-L-proline.

(b) [1(S)]-1-[3-(Acetyloxy)-2-methyl-1-oxopropyl]-4-hydroxy-4-(4-[(4-pyridyl)methyl]-L-proline The N-carbobenzyloxy-4-hydroxy-4-[(4-pyridyl)methyl]-L-proline from part (a) is hydrogenated according to the procedure of Example 1 (b) to yield 4-hydroxy-4-[(4-pyridyl)methyl]-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-[(4-pyridyl)methyl]-L-proline.

(c) [1(S)]-4-Hydroxy-1-(3-mercapto-2-methyl-1-oxopropyl)-4-[(4-pyridyl)methyl]-L-proline The product from part (b) is treated with concentrated ammonia according to the procedure of Example 2 to yield [1(S)]-4-hydroxy-1-(3-mercapto-2-methyl-1-oxopropyl)-4-[(4-pyridyl)methyl]-L-proline.

EXAMPLE 46

[1(S),2S]-2,5-Dihydro-1-(3-mercapto-2-methyl-1-oxopropyl)-4-[(4-pyridyl)methyl]-1H-pyrrole-2-carboxylic acid (a) 3,4-Dehydro-4-[(4-pyridyl)methyl]-L-proline The N-carbobenzyloxy-4-hydroxy-4-[(4-pyridyl)methyl]-L-proline from Example 45 (a) is treated with hydrochloric acid according to the procedure of Example 3 (a) to yield 3,4-dehydro-4-[(4-pyridyl)methyl]-L-proline.

(b) [1(S),2S]-1-[3-(Acetylthio)-2-methyl-1-oxopropyl]-2,5-dihydro-4-[(4-pyridyl)methyl]-1H-pyrrole-2-carboxylic acid The 3,4-dehydro-4-[(4-pyridyl)methyl]-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-[(4-pyridyl)-methyl]-1H-pyrrole-2-carboxylic acid.

(c) [1(S),2S]-2,5-Dihydro-1-(3-mercapto-2-methyl-1-oxopropyl)-4-[(4-pyridyl)methyl]-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-[(4-pyridyl)methyl]-1H-pyrrole-2-carboxylic acid.

EXAMPLE 47

[1(S)]-4-Hydroxy-1-(3-mercapto-3-methyl-1-oxopropyl)-4-(3-pyridyl)-L-proline (a) N-Carbobenzyloxy-4-hydroxy-4-(3-pyridyl)-L-proline Following the procedure of Example 1 (a) but substituting an equivalent amount of (3-pyridyl) magnesium bromide for the phenylmagnesium bromide one obtains N-carbobenzyloxy-4-hydroxy-4-(3-pyridyl)-L-proline.

(b) [1(S)]-1-[3-(Acetylthio)-3-methyl-1-oxopropyl]-4-hydroxy-4-(3-pyridyl)-L-proline The N-carbobenzyloxy-4-hydroxy-4-(3-pyridyl)-L-proline from part (a) is hydrogenated according to the procedure of Example 1 (b) to yield 4-hydroxy-4-(3-pyridyl)-L-proline. This amino acid is reacted with D-3-acetylthio-3-methylpropionyl chloride according to the procedure of Example 1 (c) to yield [1(S)]-1-[3-(acetylthio)-3-methyl-1-oxopropyl]-4-hydroxy-4-(3-pyridyl)-L-proline.

(c) [1(S)]-4-Hydroxy-1-(3-mercapto-3-methyl)-1-oxypropyl)-4-(3-pyridyl)-L-proline The product from part (b) is treated with concentrated ammonia according to the procedure of Example 2 to yield [1(S)]-4-hydroxy-1-(3-mercapto-3-methyl-1-oxopropyl)-4-(3-pyridyl)-L-proline.

EXAMPLE 48

[1(S),2S]-2,5-Dihydro-1-(3-mercapto-3-methyl-1-oxopropyl)-4-(3-pyridyl)-1H-pyrrole-2-carboxylic acid (a) 3,4-Dehydro-4-(3-pyridyl)-L-proline The N-carbobenzyloxy-4-hydroxy-4-(3-pyridyl)-L-proline from Example 47 (a) is treated with hydrochloric acid according to the procedure of Example 3 (a) to yield 3,4-dehydro-4-(3-pyridyl)-L-proline.

(b) [1(S),2S]-1-[3-(Acetylthio)-3-methyl-1-oxopropyl]-2,5-dihydro-4-(3-pyridyl)-1H-pyrrole-2-carboxylic acid The 3,4-dehydro-4-(3-pyridyl)-L-proline from part (a) is reacted with D-3-acetylthio-3-methylpropionyl chloride according to the procedure of Example 3 (b) to yield [1(S),2S]-1-[3-(acetylthio)-3-methyl-1-oxopropyl]-2,5-dihydro-4-(3-pyridyl)-1H-pyrrole-2-carboxylic acid.

(c) [1(S),2S]-2,5-Dihydro-1-(3-mercapto-3-methyl-1-oxopropyl)-4-(3-pyridyl)-1H-pyrrole-2-carboxylic acid The product from part (b) is treated with concentrated ammonia according to the procedure of Example 4 to yield [1(S),2S]-2,5-dihydro-1-(3-mercapto-3-methyl-1-oxopropyl)-4-(3-pyridyl)-1H-pyrrole-2-carboxylic acid.

EXAMPLE 49

[1(S)]-4-Ethenyl-4-hydroxy-1-(3-mercapto-2-methyl-1-oxopropyl)-L-proline (a) N-Carbobenzyloxy-4-ethenyl-4-hydroxy-L-proline Following the procedure of Example 1(a) but substituting an equivalent amount of ethenylmagnesium bromide for the phenylmagnesium bromide one obtains N-carbobenzyloxy-4-ethenyl-4-hydroxy-L-proline.

(b)
[1(S)]-1-[3-(Acetylthio)-2-methyl-1-oxopropyl]-4-ethenyl-4-hydroxy-L-proline The N-carbobenzyloxy-4-ethenyl-4-hydroxy-L-proline from part (a) is hydrogenated according to the procedure of Example 1(b) to yield 4-ethenyl-4-hydroxy-L-proline. This amino acid is reacted with D-3-acetylthio-2-methylpropionyl chloride according to the procedure of Example 1(c) to yield [1(S)]-1-[3-(acetylthio)-2-methyl-1-oxopropyl]-4-ethenyl-4-hydroxy-L-proline.

(c)
[1(S)]-4-Ethenyl-4-hydroxy-1-(3-mercapto-2-methyl-1-oxopropyl)-L-proline

The product from part (b) is treated with concentrated ammonia according to the procedure of Example 2 to yield [1(S)]-4-ethenyl-4-hydroxy-1-(3-mercapto-2-methyl-1-oxopropyl)-L-proline.

EXAMPLE 50

[1(S),2S]-2,5-Dihydro-4-ethenyl-1-(3-mercapto-2-methyl-1-oxopropyl)-1H-pyrrole-2-carboxylic acid (a) 3,4-Dehydro-4-ethenyl-L-proline The N-carbobenzyloxy-4-ethenyl-4-hydroxy-L-proline from Example 49(a) is treated with hydrochloric acid according to the procedure of Example 3(a) to yield 3,4-dehydro-4-ethenyl-L-proline.

(b)
[1(S),2S]-1-[3-(Acetylthio)-2-methyl-1-oxopropyl]-2,5-dihydro-4-ethenyl-1H-pyrrole-2-carboxylic acid The 3,4-dehydro-4-ethenyl-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-ethenyl-1H-pyrrole-2-carboxylic acid.

(c)
[1(S),2S]-2,5-Dihydro-4-ethenyl-1-(3-mercapto-2-methyl-1-oxopropyl)-1H-pyrrole-2-carboxylic acid The product from part (b) is treated with concentrated ammonia according to the procedure of Example 4 to yield [1(S),2S]-2,5-dihydro-4-ethenyl-1-(3-mercapto-2-methyl-1-oxopropyl)-1H-pyrrole-2-carboxylic acid.

EXAMPLE 51

4-Allyl-4-Hydroxy-1-(3-mercapto-1-oxopropyl)-L-proline (a) N-Carbobenzyloxy-4-allyl-4-hydroxy-L-proline Following the procedure of Example 1(a) but substituting an equivalent amount of allylmagnesium bromide for the phenylmagnesium bromide one obtains N-carbobenzyloxy-4-allyl-4-hydroxy-L-proline.

(b)
1-[3-(Acetylthio)-1-oxopropyl]-4-allyl-4-hydroxy-L-proline

The N-carbobenzyloxy-4-allyl-4-hydroxy-L-proline from part (a) is hydrogenated according to the procedure of Example 1(b) to yield 4-allyl-4-hydroxy-L-proline. This amino acid is reacted with 3-acetylthiopropionyl chloride according to the procedure of Example 1(c) to yield 1-[3-(acetylthio)-1-oxopropyl]-4-allyl-4-hydroxy-L-proline.

(c)
4-Allyl-4-hydroxy-1-(3-mercapto-1-oxopropyl)-L-proline

The product from part (b) is treated with concentrated ammonia according to the procedure of Example 2 to yield 4-allyl-4-hydroxy-1-(3-mercapto-1-oxopropyl)-L-proline.

EXAMPLE 52

(2S)-4-Allyl-2,5-dihydro-1-(3-mercapto-1-oxopropyl)-1H-pyrrole-2-carboxylic acid (a) 3,4-Dehydro-4-allyl-L-proline The N-carbobenzyloxy-4-allyl-4-hydroxy L-proline from Example 51(a) is treated with hydrochloric acid according to the procedure of Example 3(a) to yield 3,4-dehydro-4-allyl-L-proline.

(b)
(2S)-1-[3-(Acetylthio)-1-oxopropyl]-4-allyl-2,5-dihydro-1H-pyrrole-2-carboxylic acid The 3,4-dehydro-4-allyl-L-proline from part (a) is reacted with 3-acetylthiopropionyl chloride according to the procedure of Example 3(b) to yield (2S)-1-[3-(acetylthio)-1-oxopropyl]-4-allyl-2,5-dihydro-1H-pyrrole-2-carboxylic acid.

(c)
(2S)-4-Allyl-2,5-dihydro-1-(3-mercapto-1-oxopropyl)-1H-pyrrole-2-carboxylic acid The product from part (b) is treated with concentrated ammonia according to the procedure of Example 4 to yield (2S)-4-allyl-2,5-dihydro-1-(3-mercapto-1-oxopropyl)-1H-pyrrole-2-carboxylic acid.

EXAMPLE 53

[1(S)]-4-Hydroxy-1-(3-mercapto-2-methyl-1-oxopropyl)-4-propargyl-L-proline (a)
N-Carbobenzyloxy-4-hydroxy-4-propargyl-L-proline Following the procedure of Example 5(a) but substituting an equivalent amount of propargyl lithium for the phenyl lithium one obtains N-carbobenzyloxy-4-hydroxy-4-propargyl-L-proline.

(b)
[1(S)]-1-[3-(Acetylthio)-2-methyl-1-oxopropyl]-4-hydroxy-4-propargyl-L-proline The N-carbobenzyloxy-4-hydroxy-4-propargyl-L-proline from part (a) is hydrogenated according to the procedure of Example 1(b) to yield 4-hydroxy-4-propargyl-L-proline. This amino acid is reacted with D-3-acetylthio-2-methylpropionyl chloride according to the procedure of Example 1(c) to yield [1(S)]-1-[3-(acetylthio)-2-methyl-1-oxopropyl]-4-hydroxy-4-propargyl-L-proline.

(c)
[1(S)]-4-Hydroxy-1-(3-mercapto-2-methyl-1-oxopropyl)-4-propargyl-L-proline

The product from part (b) is treated with concentrated ammonia according to the procedure of Example 2 to yield [1(S)]-4-hydroxy-1-(3-mercapto-2-methyl-1-oxopropyl)-4-propargyl-L-proline.

EXAMPLE 54

[1(S),2S]-2,5-Dihydro-1-(3-mercapto-2-methyl-1-oxopropyl)-4-propargyl-1H-pyrrole-2-carboxylic acid (a) 3,4-Dehydro-4-propargyl-L-proline The N-carbobenzyloxy-4-hydroxy-4-propargyl-L-proline from Example 53 (a) is treated with hydrochloric acid according to the procedure of Example 3(a) to yield 3,4-dehydro-4-propargyl-L-proline.

(b) [1(S),2S]-1-[3-(Acetylthio)-2-methyl-1-oxopropyl]-2,5-dihydro-4-propargyl-1H-pyrrole-2-carboxylic acid The 3,4-dehydro-4-propargyl-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-propargyl-1H-pyrrole-2-carboxylic acid.

(c) [1(S),2S]-2,5-Dihydro-1-(3-mercapto-2-methyl-1-oxopropyl)-4-propargyl-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-propargyl-1H-pyrrole-2-carboxylic acid.

EXAMPLE 55

[1(S)]-4-Ethynyl-4-hydroxy-1-(3-mercapto-2-methyl-1-oxopropyl)-L-proline (a) N-Carbobenzyloxy-4-ethynyl-4-hydroxy-L-proline Following the procedure of Example 5(a) but substituting an equivalent amount of ethynyl lithium for the phenyl lithium one obtains N-carbobenzyloxy-4-ethynyl-4-hydroxy-L-proline.

(b) [1(S)]-1-[3-(Acetylthio)-2-methyl-1-oxopropyl]-4-ethynyl-4-hydroxy-L-proline The N-carbobenzyloxy-4-ethynyl-4-hydroxy-L-proline from part (a) is hydrogenated according to the procedure of Example 1 (b) to yield 4-ethynyl-4-hydroxy-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-ethynyl-4-hydroxy-L-proline.

(c) [1(S)]-4-Ethynyl-4-hydroxy-1-(3-mercapto-2-methyl-1-oxopropyl-L-proline

The product from part (b) is treated with concentrated ammonia according to the procedure of Example 2 to yield [1(S)]-4-ethynyl-4-hydroxy-1-(3-mercapto-2-methyl-1-oxopropyl)-L-proline.

EXAMPLE 56

[1(S),2S]-2,5-Dihydro-4-ethynyl-1-(3-mercapto-2-methyl-1-oxopropyl)-1H-pyrrole-2-carboxylic acid (a) 3,4-Dehydro-4-ethynyl-L-proline The N-carbobenzyloxy-4-ethynyl-4-hydroxy-L-proline from Example 55 (a) is treated with hydrochloric acid according to the procedure of Example 3 (a) to yield 3,4-dehydro-4-ethynyl-L-proline.

(b) [1(S),2S]-1-[3-(Acetylthio)-2-methyl-1-oxopropyl]-2,5-dihydro-4-ethynyl-1H-pyrrole-2-carboxylic acid The 3,4-dehydro-4-ethynyl-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-ethynyl-1H-pyrrole-2-carboxylic acid.

(c) [1(S),2S]-2,5-Dihydro-4-ethynyl-1-(3-mercapto-2-methyl-1-oxopropyl)-1H-pyrrole-2-carboxylic acid The product from part (b) is treated with concentrated ammonia according to the procedure of Example 4 to yield [1(S),2S]-2,5-dihydro-4-ethynyl-1-(3-mercapto-2-methyl-1-oxopropyl)-1H-pyrrole-2-carboxylic acid.

EXAMPLE 57

[1(S)]-4-Cyclohexyl-4-hydroxy-1-(3-mercapto-2-methyl-1-oxopropyl)-L-proline (a) N-Carbobenzyloxy-4-cyclohexyl-4-hydroxy-L-proline Following the procedure of Example 1 (a) but substituting an equivalent amount of cyclohexylmagnesium chloride for the phenylmagnesium bromide one obtains N-carbobenzyloxy-4-cyclohexyl-4-hydroxy-L-proline.

(b) [1(S)]-1-[3-(Acetylthio)-2-methyl-1-oxopropyl]-4-cyclohexyl-4-hydroxy-L-proline The N-carbobenzyloxy-4-cyclohexyl-4-hydroxy-L-proline from part (a) is hydrogenated according to the procedure of Example 1 (b) to yield 4-cyclohexyl-4-hydroxy-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-cyclohexyl-4-hydroxy-L-proline.

(c) [1(S)]-4-Cyclohexyl-4-hydroxy-1-(3-mercapto-2-methyl-1-oxopropyl)-L-proline

The product from part (b) is reacted with concentrated ammonia according to the procedure of Example 2 to yield [1(S)]-4-cyclohexyl-4-hydroxy-1-(3-mercapto-2-methyl-1-oxopropyl)-L-proline.

EXAMPLE 58

[1(S),2S]-4-Cyclohexyl-2,5-dihydro-1-(3-mercapto-2-methyl-1-oxopropyl)-1H-pyrrole-2-carboxylic acid (a) 4-Cyclohexyl-3,4-dehydro-L-proline The N-carbobenzyloxy-4-cyclohexyl-4-hydroxy-L-proline from Example 57 (a) is treated with hydrochloric acid according to the procedure of Example 3 (a) to yield 4-cyclohexyl-3,4-dehydro-L-proline.

(b) [1(S),2S]-1-[3-(Acetylthio)-2-methyl-1-oxopropyl]-4-cyclohexyl-2,5-dihydro-1H-pyrrole-2-carboxylic acid The 4-cyclohexyl-3,4-dehydro-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-4-cyclohexyl-2,5-dihydro-1H-pyrrole-2-carboxylic acid.

(c)
[1(S),2S]-4-Cyclohexyl-2,5-dihydro-1-(3-mercapto-2-methyl-1-oxopropyl)-1H-pyrrole-2-carboxylic acid The product from part (b) is treated with concentrated ammonia according to the procedure of Example 4 to yield [1(S),2S]-4-cyclohexyl-2,5-dihydro-1-(3-mercapto-2-methyl-1-oxopropyl)-1H-pyrrole-2-carboxylic acid.

EXAMPLE 59

4-Hydroxy-1-(3-mercapto-1-oxopropyl)-4-(phenylpropyl)-L-proline (a)
N-Carbobenzyloxy-4-hydroxy-4-(phenylpropyl)-L-proline Following the procedure of Example 1 (a) but substituting an equivalent amount of (phenylpropyl) magnesium bromide for the phenylmagnesium bromide one obtains N-carbobenzyloxy-4-hydroxy-4-(phenylpropyl)-L-proline.

(b)
1-[3-(Acetylthio)-1-oxopropyl]-4-hydroxy-4-(phenylpropyl)-L-proline

The N-carbobenzyloxy-4-hydroxy-4-(phenylpropyl)-L-proline from part (a) is hydrogenated according to the procedure of Example 1 (b) to yield 4-hydroxy-4-(phenylpropyl)-L-proline. This amino acid is reacted with 3-acetylthiopropionyl chloride according to the procedure of Example 1 (c) to yield 1-[3-(acetylthio)-1-oxopropyl]-4-hydroxy-4-(phenylpropyl)-L-proline.

(c)
4-Hydroxy-1-(3-mercapto-1-oxopropyl)-4-(phenylpropyl)-L-proline

The product from part (b) is treated with concentrated ammonia according to the procedure of Example 2 to yield 4-hydroxy-1-(3-mercapto-1-oxopropyl)-4-(phenylpropyl)-L-proline.

EXAMPLE 60

[2S]-2,5-Dihydro-1-(3-mercapto-1-oxopropyl)-4-(phenylpropyl)-1H-pyrrole-2-carboxylic acid (a) 3,4-Dehydro-4-(phenylpropyl)-L-proline The N-carbobenzyloxy-4-hydroxy-4-(phenylpropyl)-L-proline from Example 59 (a) is treated with hydrochloric acid according to the procedure of Example 3 (a) to yield 3,4-dehydro-4-(phenylpropyl)-L-proline.

(b)
[2S]-1-[3-(Acetylthio)-1-oxopropyl]-2,5-dihydro-4-(phenylpropyl)-1H-pyrrole-2-carboxylic acid The 3,4-dehydro-4-(phenylpropyl)-L-proline from part (a) is reacted with 3-acetylthiopropionyl chloride according to the procedure of Example 3 (b) to yield [2S]-1-[3-(acetylthio)-1-oxopropyl]-2,5-dihydro-4-(phenylpropyl)-1H-pyrrole-2-carboxylic acid.

(c)
[2S]-2,5-Dihydro-1-(3-mercapto-1-oxopropyl)-4-(phenylpropyl)-1H-pyrrole-2-carboxylic acid The product from part (b) is treated with concentrated ammonia according to the procedure of Example 4 to yield [2S]-2,5-dihydro-1-(3-mercapto-1-oxopropyl)-4-(phenylpropyl)-1H-pyrrole-2-carboxylic acid.

EXAMPLE 61

[1(S)]-4-Hydroxy-1-(3-mercapto-2-methyl-1-oxopropyl)-4-(α-naphthyl)-L-proline (a)
N-Carbobenzyloxy-4-hydroxy-4-(α-naphthyl)-L-proline Following the procedure of Example 1 (a) but substituting an equivalent amount of α-naphthylmagnesium bromide for the phenylmagnesium bromide one obtains N-carbobenzyloxy-4-hydroxy-4-(α-naphthyl)-L-proline.

(b)
[1(S)]-1-[3-(Acetylthio)-2-methyl-1-oxopropyl]-4-hydroxy-4-(α-naphthyl)-L-proline The N-carbobenzyloxy-4-hydroxy-4-(α-naphthyl)-L-proline from part (a) is hydrogenated according to the procedure of Example 1 (b) to yield 4-hydroxy-4-(α-naphthyl)-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-(α-naphthyl)-L-proline.

(c)
[1(S)]-4-Hydroxy-1-(3-mercapto-2-methyl-1-oxopropyl)-4-(α-naphthyl)-L-proline The product from part (b) is reacted with concentrated ammonia according to the procedure of Example 2 to yield [1(S)]-4-hydroxy-1-(3-mercapto-2-methyl-1-oxopropyl)-4-(α-mercapto)-L-proline.

EXAMPLE 62

[1(S),2S]-2,5-Dihydro-1-(3-mercapto-2-methyl-1-oxopropyl)-4-(α-naphthyl)-1H-pyrrole-2-carboxylic acid (a) 3,4-Dehydro-4-(α-naphthyl)-L-proline The N-carbobenzyloxy-4-hydroxy-4-(α-naphthyl)-L-proline from Example 61 (a) is treated with hydrochloric acid according to the procedure of Example 3 (a) to yield 3,4-dehydro-4-(α-naphthyl)-L-proline.

(b)
[1(S),2S]-1-[3-(Acetylthio)-2-methyl-1-oxopropyl]-2,5-dihydro-4-(α-naphthyl)-1H-pyrrole-2-carboxylic acid The 3,4-dehydro-4-(α-naphthyl)-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-(α-naphthyl)-1H-pyrrole-2-carboxylic acid.

(c)
[1(S),2S]-2,5-Dihydro-1-(3-mercapto-2-methyl-1-oxopropyl)-4-(α-naphthyl)-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-(α-naphthyl)-1H-pyrrole-2-carboxylic acid.

EXAMPLE 63

[1(S)]-4-Hydroxy-1-(3-mercapto-2-methyl-1-oxopropyl)-4-(β-naphthyl)-L-proline (a)

N-Carbobenzyloxy-4-hydroxy-4-(β-naphthyl)-L-proline

Following the procedure of Example 1 (a) but substituting an equivalent amount of β-naphthyl magnesium bromide for the phenylmagnesium bromide one obtains N-carbobenzyloxy-4-hydroxy-4-(β-naphthyl)-L-proline.

(b)

[1(S)]-1-[3-(Acetylthio)-2-methyl-1-oxopropyl]-4-hydroxy-4-(β-naphthyl)-L-proline The N-carbobenzyloxy-4-hydroxy-4-(β-naphthyl)-L-proline from part (a) is hydrogenated according to the procedure of Example 1 (b) to yield 4-hydroxy-4-(β-naphthyl)-L-proline. This amino acid is reacted with D-3-acetylthio-2-methylpropionyl chloride according to the procedure of Example 1 (c) to yield [1(S)]-1-[3-(acetylthio)-2-methyl-1-oxopropyl]-4-hydroxy-4-(β-naphthyl)-L-proline.

(c)

[1(S)]-4-Hydroxy-1-(3-mercapto-2-methyl-1-oxopropyl)-4-(β-naphthyl)-L-proline

The product from part (b) is reacted with concentrated ammonia according to the procedure of Example 2 to yield [1(S)]-4-hydroxy-1-(3-mercapto-2-methyl-1-oxopropyl)-4-(β-naphthyl)-L-proline.

EXAMPLE 64

[1(S),2S]-2,5-Dihydro-1-(3-mercapto-2-methyl-1-oxopropyl)-4-(β-naphthyl)-1H-pyrrole-2-carboxylic acid (a) 3,4-Dehydro-4-(β-naphthyl)-L-proline The N-carbobenzyloxy-4-hydroxy-4-(β-naphthyl)-L-proline from Example 63 (a) is treated with hydrochloric acid according to the procedure of Example 3 (a) to yield 3,4-dehydro-4-(β-naphthyl)-L-proline.

(b)

[1(S),2S]-1-[3-(Acetylthio)-2-methyl-1-oxopropyl]-2,5-dihydro-4-(β-naphthyl)-1H-pyrrole-2-carboxylic acid The 3,4-dehydro-4-(β-naphthyl)-L-proline from part (a) is reacted with D-3-acetylthio-2-methylpropionyl chloride according to the procedure of Example 3 (b) to yield [1(S),2S]-1-[3-(acetylthio)-2-methyl-1-oxopropyl]-2,5-dihydro-4-(β-naphthyl)-1H-pyrrole-2-carboxylic acid.

(c)

[1(S),2S]-2,5-Dihydro-1-(3-mercapto-2-methyl-1-oxopropyl)-4-(β-naphthyl)-1H-pyrrole-2-carboxylic acid The product from part (b) is treated with concentrated ammonia according to the procedure of Example 4 to yield [1(S),2S]-2,5-dihydro-1-(3-mercapto-2-methyl-1-oxopropyl)-4-(β-naphthyl)-1H-pyrrole-2-carboxylic acid.

EXAMPLES 65–72

Following the procedure of Example 1 (b) but substituting for the D-3-acetylthio-2-methylpropionyl chloride the acid chloride listed below in Col. I one obtains the acylmercapto product listed below in Col. II.

| Column I | Column II |
| --- | --- |
| D-3-benzoylthio-2-methylpropionyl chloride | [1(S),4R]-1-[3-(benzoylthio)-2-methyl-1-oxopropyl]-4-hydroxy-4-phenyl-L-proline |
| D-3-[[(2-thienyl)carbonyl]thio]-2-methylpropionyl chloride | [1(S),4R]-1-[3-[[(2-thienyl)carbonyl]thio]-2-methyl-1-oxopropyl]-4-hydroxy-4-phenyl-L-proline |
| D-3-[[(2,2,2-trichloroethyl)carbonyl]thio]-2-methylpropionyl chloride | [1(S),4R]-1-[3-[[(2,2,2-trichloroethyl)carbonyl]thio]-2-methyl-1-oxopropyl]-4-hydroxy-4-phenyl-L-proline |
| D-3-[[(2-furyl)carbonyl]thio]-2-methylpropionyl chloride | [1(S),4R]-1-[3-[[(2-furyl)carbonyl]thio]-2-methyl-1-oxopropyl]-4-hydroxy-4-phenyl-L-proline |
| D-3-[[(4-pyridyl)carbonyl]thio]-2-methylpropionyl chloride | [1(S),4R]-1-[3-[[(4-pyridyl)carbonyl]thio]-2-methyl-1-oxopropyl]-4-hydroxy-4-phenyl-L-proline |
| D-3-[[(4-methylphenyl)carbonyl]thio]-2-methylpropionyl chloride | [1(S),4R]-1-[3-[[(4-methylphenyl)carbonyl]thio]-2-methyl-1-oxopropyl]-4-hydroxy-4-phenyl-L-proline |
| 2-[[(phenylmethyl)carbonyl]thio]acetyl chloride | (4R)-1-[2-[[(phenylmethyl)carbonyl]thio]-1-oxoethyl]-4-hydroxy-4-phenyl-L-proline |
| 3-benzoylthiopropionyl chloride | (4R)-1-[3-(benzoylthio)-1-oxopropyl]-4-hydroxy-4-phenyl-L-proline |

EXAMPLES 73–79

Following the procedure of Example 3(b) but substituting for the D-3-acetylthio-2-methylpropionyl chloride the acid chloride listed below in Col. I one obtains the acylmercapto product listed below in Col. II.

| Col. I | Col. II |
| --- | --- |
| D-3-benzoylthio-2-methylpropionyl chloride | [1(S),2S]-1-[3-(benzoylthio)-2-methyl-1-oxopropyl]-2,5-dihydro-4-phenyl-1H—pyrrole-2-carboxylic acid |
| 3-benzoylthiopropionyl chloride | (2S)-1-[3-(benzoylthio)-1-oxopropyl]-2,5-dihydro-4-phenyl-1H—pyrrole-2-carboxylic acid |
| D-3-[[(2,2,2-trichloroethyl)carbonyl]thio]-2-methylpropionyl chloride | [1(S),2S]-1-[3-[[(2,2,2-trichloroethyl)carbonyl]thio]-2-methyl-1-oxopropyl]-2,5-dihydro-4-phenyl-1H—pyrrole-2-carboxylic acid |
| 2-[[(2-thienyl)carbonyl]thio]acetyl chloride | (2S)-1-[2-[[(2-thienyl)carbonyl]thio]-1-oxoethyl]-2,5-dihydro-4-phenyl-1H—pyrrole-2-carboxylic acid |
| D-3-[[(2-furyl)carbonyl]thio]-2-methylpropionyl chloride | [1(S),2S]-1-[3-[[(2-furyl)carbonyl]thio]-2-methyl-1-oxopropyl]-2,5-dihydro-4-phenyl-1H—pyrrole-2-carboxylic acid |
| D-3-[[(3-pyridyl)carbonyl]thio]-2-methylpropionyl chloride | [1(S),2S]-1-[3-[[(3-pyridyl)carbonyl]thio]-2-methyl-1-oxopropyl]-2,5-dihydro-4-phenyl-1H—pyrrole-2-carboxylic acid |
| D-3-[[[(4-methoxyphenyl)methyl]carbonyl]thio]-2-methylpropionyl chloride | [1(S),2S]-1-[3-[[[(4-methoxyphenyl)methyl]carbonyl]thio]-2-methyl-1-oxopropyl]-2,5-dihydro-4-phenyl-1H—pyrrole-2-carboxylic acid |

EXAMPLE 80

[1(S),1'(S),4R,4'R]-1,1'-[Dithiobis(2-methyl-1-oxopropane-3,1-diyl)]bis[4-hydroxy-4-phenyl-L-proline]

A solution of the product from Example 2 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent evaporated to give [1(S),1'(S),4R,4'R]-1,1'-[dithiobis(2-methyl-1-oxopropane-3,1-diyl)]bis[4-hydroxy-4-phenyl-L-proline].

EXAMPLE 81

[1(S),1'(S),2S,2'S]-1,1'-[Dithiobis[2-methyl-1-oxopropane-3,1-diyl)]bis[4-phenyl-1H-pyrrole-2-carboxylic acid]

A solution of the product from Example 4 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent evaporated to give [1(S),1'(S),2S,2'S]-1,1'-[dithiobis(2-methyl-1-oxopropane-3,1-diyl)]bis[4-phenyl-1H-pyrrole-2-carboxylic acid].

EXAMPLE 82

[1(S),4R]-1-[3-(Acetylthio)-2-methyl-1-oxopropyl]-4-hydroxy-4-phenyl-L-proline, methyl ester A solution of the product from Example 1 in ether is treated with a slight excess of diazomethane. After standing at room temperature, the solvent is evaporated to give [1(S),4R]-1-[3-(acetylthio)-2-methyl-1-oxopropyl]-4-hydroxy-4-phenyl-L-proline, methyl ester.

EXAMPLE 83

[1(S),2S]-1-[3-(Acetylthio)-2-methyl-1-oxopropyl]-2,5-dihydro-4-phenyl-1H-pyrrole-2-carboxylic acid, methyl ester A solution of the product from Example 3 in ether is treated with a slight excess of diazomethane. After standing at room temperature, the solvent is evaporated to give [1(S),2S]-1-[3-(acetylthio)-2-methyl-1-oxopropyl]-2,5-dihydro-4-phenyl-1H-pyrrole-2-carboxylic acid, methyl ester.

EXAMPLE 84

[1(S),4R]-4-Hydroxy-1-(3-mercapto-2-methyl-1-oxopropyl)-4-phenyl-L-proline, methyl ester The methyl ester product from Example 82 is treated with concentrated ammonia according to the procedure of Example 2 to give [1(S),4R]-4-hydroxy-1-(3-mercapto-2-methyl-1-oxopropyl)-4-phenyl-L-proline, methyl ester.

EXAMPLE 85

[1(S),2S]-2,5-Dihydro-1-(3-mercapto-2-methyl-1-oxopropyl)-4-phenyl-1H-pyrrole-2-carboxylic acid, methyl ester The methyl ester product from Example 83 is treated with concentrated ammonia according to the procedure of Example 4 to give [1(S),2S]-2,5-dihydro-1-(3-mercapto-2-methyl-1-oxopropyl)-4-phenyl-1H-pyrrole-2-carboxylic acid, methyl ester.

EXAMPLE 86

[1(S),4R]-4-Hydroxy-1-(3-mercapto-2-methyl-1-oxopropyl)-4-phenyl-L-proline, sodium salt An aqueous solution of the product from Example 2 is treated with a slight excess of sodium bicarbonate. The solution is lyophilized to yield [1(S),4R]-4-hydroxy-1-(3-mercapto-2-methyl-1-oxopropyl)-4-phenyl-L-proline, sodium salt.

EXAMPLE 87

[1(S),2S]-2,5-Dihydro-1-(3-mercapto-2-methyl-1-oxopropyl)-4-phenyl-1H-pyrrole-2-carboxylic acid, sodium salt An aqueous solution of the product from Example 4 is treated with a slight excess of sodium bicarbonate. The solution is lyophilized to yield [1(S),2S]-2,5-dihydro-1-(3-mercapto-2-methyl-1-oxopropyl)-4-phenyl-1H-pyrrole-2-carboxylic acid, sodium salt.

EXAMPLE 88

1000 tablets each containing the following ingredients:

| | |
|---|---|
| [1(S),2S]-2,5-Dihydro-1-(3-mercapto-2-methyl-1-oxopropyl)-4-phenyl-1H—pyrrole-2-carboxylic acid | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared (from sufficient bulk quantities) by mixing the [1(S),2S]-2,5-dihydro-1-(3-mercapto-2-methyl-1-oxopropyl)-4-phenyl-1H-pyrrole-2-carboxylic acid and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

EXAMPLE 89

Tablets each containing 100 mg. of [1(S),4R]-4-hydroxy-1-(3-mercapto-2-methyl-1-oxopropyl)-4-phenyl-L-proline are produced as described in Example 88.

EXAMPLE 90

1000 tablets each containing the following ingredients:

| | |
|---|---|
| [1(S),2S]-1-[3-(Acetylthio)-2-methyl-1-oxopropyl]-2,5-dihydro-4-phenyl-1H—pyrrole-2-carboxylic acid | 50 mg. |
| Lactose | 25 mg. |
| Avicel | 38 mg. |
| Cornstarch | 15 mg. |
| Magnesium stearate | 2 mg. |
| | 130 mg. | are prepared by admixing the [1(S),2S]-1-[3-(acetylthio)-2-methyl-1-oxopropyl]-2,5-dihydro-4-phenyl-1H-pyrrole-2-carboxylic acid, lactose and Avicel and then blending with the corn starch. Magnesium stearate is added. The dry mixture is compressed in a tablet press to form 1000 130 mg. tablets each containing 50 mg. of active ingredient. The tablets are coated with a solution of Methocel E 15 (methyl cellulose) including as a color a lake containing yellow #6.

EXAMPLE 91

Tablets each containing 50 mg. of [1(S),4R]-1-[3-(acetylthio)-2-methyl-1-oxopropyl]-4-hydroxy-4-phenyl-L-proline are produced as described in Example 90.

EXAMPLE 92

Two piece #1 gelatin capsules each containing 100 mg. of [1(S),2S]-2,5-dihydro-1-(3-mercapto-2-methyl-1-oxopropyl)-4-phenyl-1H-pyrrole-2-carboxylic acid, sodium salt, are filled with a mixture of the following ingredients:

| | |
|---|---|
| [1(S),2S]-2,5-Dihydro-1-(3-mercapto-2-methyl-1-oxo-propyl)-4-phenyl-1H—pyrrole-2-carboxylic acid, sodium salt | 100 mg. |
| Magnesium stearate | 7 mg. |
| Lactose | 193 mg. |

EXAMPLE 93

Gelatin capsules containing 100 mg. of [1(S),4R]-4-hydroxy-1-(3-mercapto-2-methyl-1-oxopropyl)-4-phenyl-L-proline are produced as described in Example 92.

EXAMPLE 94

An injectable solution is produced as follows:

| | |
|---|---|
| [1(S),2S]-2,5-Dihydro-1-(3-mercapto-2-methyl-1-oxopropyl)-4-phenyl-1H—pyrrole-2-carboxylic acid | 500 g. |
| Methyl paraben | 5 g. |
| Propyl paraben | 1 g. |
| Sodium chloride | 25 g. |
| Water for injection qs. | 5 l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

EXAMPLE 95

An injectable solution containing [1(S),4R]-4-hydroxy-1-(3-mercapto-2-methyl-1-oxopropyl)-4-phenyl-L-proline is prepared as described in Example 94.

EXAMPLE 95

6000 tablets each containing the following ingredients:

| | |
|---|---|
| [1(S),2S]-2,5-Dihydro-1-(3-mercapto-2-methyl-1-oxopropyl)-4-phenyl-1H—pyrrole-2-carboxylic acid | 100 mg. |
| Avicel (microcrystalline cellulose) | 100 mg. |
| Hydrochlorothiazide | 12.5 mg. |
| Lactose U.S.P. | 113 mg. |
| Corn starch U.S.P. | 17.5 mg. |
| Stearic acid U.S.P. | 7 mg. |
| | 350 mg. | are produced from sufficient bulk quantities by slugging the [1(S),2S]-2,5-dihydro-1-(3-mercapto-2-methyl-1-oxopropyl)-4-phenyl-1H-pyrrole-2-carboxylic acid, Avicel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

EXAMPLE 96

Tablets containing [1(S),4R]-4-hydroxy-(3-mercapto-2-methyl-1-oxopropyl)-4-phenyl-L-proline and hydrochlorothiazide can be prepared as described in Example 95.

The products of Examples 5 to 87 can also be formulated according to procedures of Examples 88 to 96.

What is claimed is:

1. A compound of the formula $$\begin{array}{c} R_1 \\ | \\ H_2C-C=CH \\ | \quad\quad | \\ HN\text{------}C\text{---}COOR \\ | \quad (L) \\ H \end{array}$$

wherein
R is hydrogen or lower alkyl of 1 to 7 carbons;
$R_1$ is lower alkenyl of 2 to 7 carbons, lower alkynyl of 2 to 7 carbons, $$-(CH_2)_m-\phenyl-R_6,$$

—$(CH_2)_m$-cycloalkyl wherein said cycloalkyl ring is of 3 to 7 carbons, α-naphthyl, β-naphthyl, $$-(CH_2)_m-\text{ring-}X$$

wherein said —$(CH_2)_m$-bridge is attached to an available carbon atom, or $$-(CH_2)_m-\text{pyridyl}$$

wherein said —$(CH_2)_m$—bridge is attached to an available carbon atom;
$R_6$ is hydrogen, lower alkyl of 1 to 4 carbons, lower alkoxy of 1 to 4 carbons, lower alkylthio of 1 to 4 carbons, chloro, fluoro, bromo, trifluoromethyl, or hydroxy;
m is zero, one, two or three; and
X is O or S.

2. A compound of claim 1 wherein R is hydrogen.
3. The compound of claim 2 wherein $R_1$ is phenyl.

* * * * *